US010912845B2

(12) United States Patent
Lucas et al.

(10) Patent No.: US 10,912,845 B2
(45) Date of Patent: Feb. 9, 2021

(54) TREATMENT OF RETINAL DEGENERATION USING GENE THERAPY

(71) Applicant: The University of Manchester, Manchester (GB)

(72) Inventors: Robert Lucas, Manchester (GB); Paul Bishop, Manchester (GB); Jasmina Cehajic-Kapetanovic, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 15/121,283

(22) PCT Filed: Feb. 24, 2015

(86) PCT No.: PCT/GB2015/050516
§ 371 (c)(1),
(2) Date: Aug. 24, 2016

(87) PCT Pub. No.: WO2015/128624
PCT Pub. Date: Sep. 3, 2015

(65) Prior Publication Data
US 2016/0361437 A1 Dec. 15, 2016

(30) Foreign Application Priority Data
Feb. 25, 2014 (GB) .................................. 1403260.1

(51) Int. Cl.
*A61K 48/00* (2006.01)
*A61K 38/17* (2006.01)
*A61K 38/51* (2006.01)
*A61K 31/7088* (2006.01)
*C07K 14/72* (2006.01)
*C12N 9/88* (2006.01)
*A61K 9/00* (2006.01)
*A61K 31/137* (2006.01)
*A61K 31/4409* (2006.01)

(52) U.S. Cl.
CPC .......... *A61K 48/005* (2013.01); *A61K 9/0048* (2013.01); *A61K 31/137* (2013.01); *A61K 31/4409* (2013.01); *A61K 31/7088* (2013.01); *A61K 38/1709* (2013.01); *A61K 38/51* (2013.01); *A61K 48/0058* (2013.01); *A61K 48/0075* (2013.01); *A61K 48/0083* (2013.01); *C07K 14/723* (2013.01); *C12N 9/88* (2013.01); *C12Y 402/02001* (2013.01); *C12Y 402/02008* (2013.01); *A61K 9/0019* (2013.01); *C12N 2750/14143* (2013.01); *C12N 2830/008* (2013.01)

(58) Field of Classification Search
None
See application file for complete search history.

(56) References Cited

U.S. PATENT DOCUMENTS

| 2011/0224145 A1 | 9/2011 | Greenberg et al. |
| 2013/0071373 A1* | 3/2013 | Zeitz .................... C12Q 1/6883 424/94.6 |
| 2017/0007720 A1* | 1/2017 | Boye .................. A61K 48/0075 |

FOREIGN PATENT DOCUMENTS

| NO | 2014/160281 A2 | 10/2014 |
| WO | 2004/009022 A2 | 1/2004 |
| WO | 2007/131180 A2 | 11/2007 |
| WO | 2007131180 A2 | 11/2007 |
| WO | 2010/011404 A2 | 1/2010 |
| WO | 2010011404 A2 | 1/2010 |
| WO | 2012/174674 A1 | 12/2012 |
| WO | 2015/128624 A1 | 9/2015 |

OTHER PUBLICATIONS

Berger et al (Human Gene Therapy, Oct. 2011, vol. 22, No. 10, pp. A75. Abstract).*
Zhang et al (ARVO Annual Meeting Abstract Search and Program Planner, May 2011, vol. 2011, pp. 1403).*
Chaffiol and Duebel, 2018, Retinal Degenerative Disease, Advances in Experimental Medicine and Biology 891, pp. 69-73.*
Fortuny and Flannery (Retinal Degenerative Disease, 2018, Advances in Experimental Medicine and Biology 891, pp. 75-81).*
PCT/GB2015/050516 International Search Report and Written Opinion dated Apr. 30, 2015; 10 pages.
GB Application No. 1403260.1 UK Intellectual Property Office Search Report dated Nov. 6, 2014; 5 pages.
Cehajic-Kapetanovic et al. Glycosidic enzymes enhance retinal transduction following intravitreal delivery of AAV2. Molecular Vision (2011). 17:1771-1783.
Dalkara et al. Inner Limiting Membrane Barriers to AAV-mediated Retinal Transduction from the Vitreous. Molecular Therapy (2009). 17(12):2096-2102.
Gruter et al. Potential Improvement of Lentiviral Gene Transfer by Weakening the Extracellular Matrix. Investigative Opthalmology & Visual Science (2004). 45, 4773. Abstract Only.
Mao et al. Gene Delivery of Wild-Type Rhodopsin Rescues Retinal Function in an Autosomal Dominant Retinitis Pigmentosa Mouse Model. Adv Exp Med Biol (2012). 723:199-205.
Palfi et al. Adeno-Associated Virus-Mediated Rhodopsin Replacement Provides Therapeutic Benefit in Mice with a Targeted Disruption of the Rhodopsin Gene. Human Gene Therapy (2010). 21:311-323.
Lin et al., Restoration of Visual Function in Retinal Degeneration Mice by Ectopic Expression of Melanopsin, 2008, PNAS, vol. 105(41), pp. 16009-16014.

(Continued)

*Primary Examiner* — Celine X Qian
(74) *Attorney, Agent, or Firm* — Linda B. Huber; Nixon Peabody LLP

(57) ABSTRACT

The present invention relates to an improved method of providing photoreceptor function to a cell, for example for use in the treatment of retinal degeneration. The present invention also relates to compositions and kits, in particular for use in such methods.

14 Claims, 22 Drawing Sheets

(56) References Cited

OTHER PUBLICATIONS

Bi et al., Ectopic Expression of a Microbial-Type Rhodopsin Restores Visual Responses in Mice with Photoreceptor Degeneration, Neuron 50, 2006, pp. 23-33.

Cehajic-Kepetanovic et al., Enhancement of Light Sensitivity in Retinal Degeneration in Mice by Use of Novel Optogenetic Approaches, The Lancet, 2014.

Cronin et al., Efficient Transduction and Optogenetic Stimulation of Retinal Bipolar Cells by a Synthetic Adeno-associated Virus Capsid and Promoter, EMBO Molecular Medicine, 2014, vol. 6(9), pp. 1175-1190.

Doroudchi et al., Virally Delivered Channelrhodopsin-2 Safely and Effectively Restores Visual Function in Multiple Mouse Models of Blindness, The American Society of Gene & Cell Therapy, 2011, vol. 19(7), pp. 1220-1229.

Lagali et al., Light-activated Channels Targeted to ON Bipolar Cells Restore Visual Function in Retinal Degeneration, Nature Neuroscience, 2008, vol. 11(6), pp. 667-675.

Lin et al., Restoration of Visual Function in Retinal Degeneration Mice by Ectopic Expression of Melanopsin, PNAS, 2008, vol. 105(41) pp. 16009-16014.

Schon et al., Retinal Gene Delivery by Adeno-Associated Virus (AAV) Vectors: Strategies and Application, European Journal of Pharmaceutics and Biopharmaceutics, 2015, pp. 343-352.

Yin et al., Intravitreal Injection of AAV2 Transduces Macaque Inner Retina, Investigative Ophthalmology & Visual Science, 2011, vol. 52(5), pp. 2775-2783.

Wikipedia page on Opsin, Difference between revisions, revision as of Feb. 24, 2014, retrieved on Jan. 28, 2020 retrieved from https:/en.wikipedia.org/w/index.php?title=Opsin&diff=prev&oldid=596947179.

\* cited by examiner

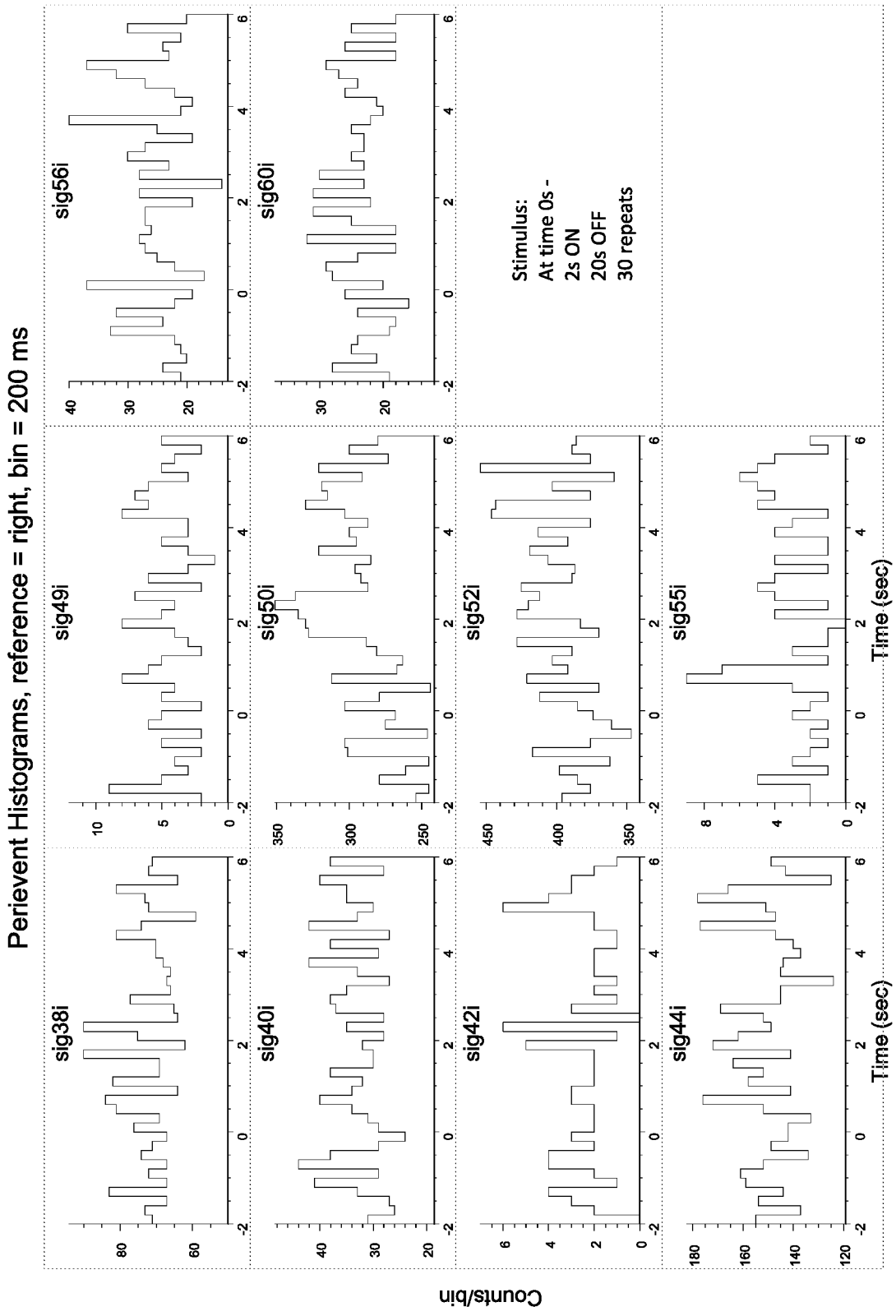
Figure 3 A) ND2

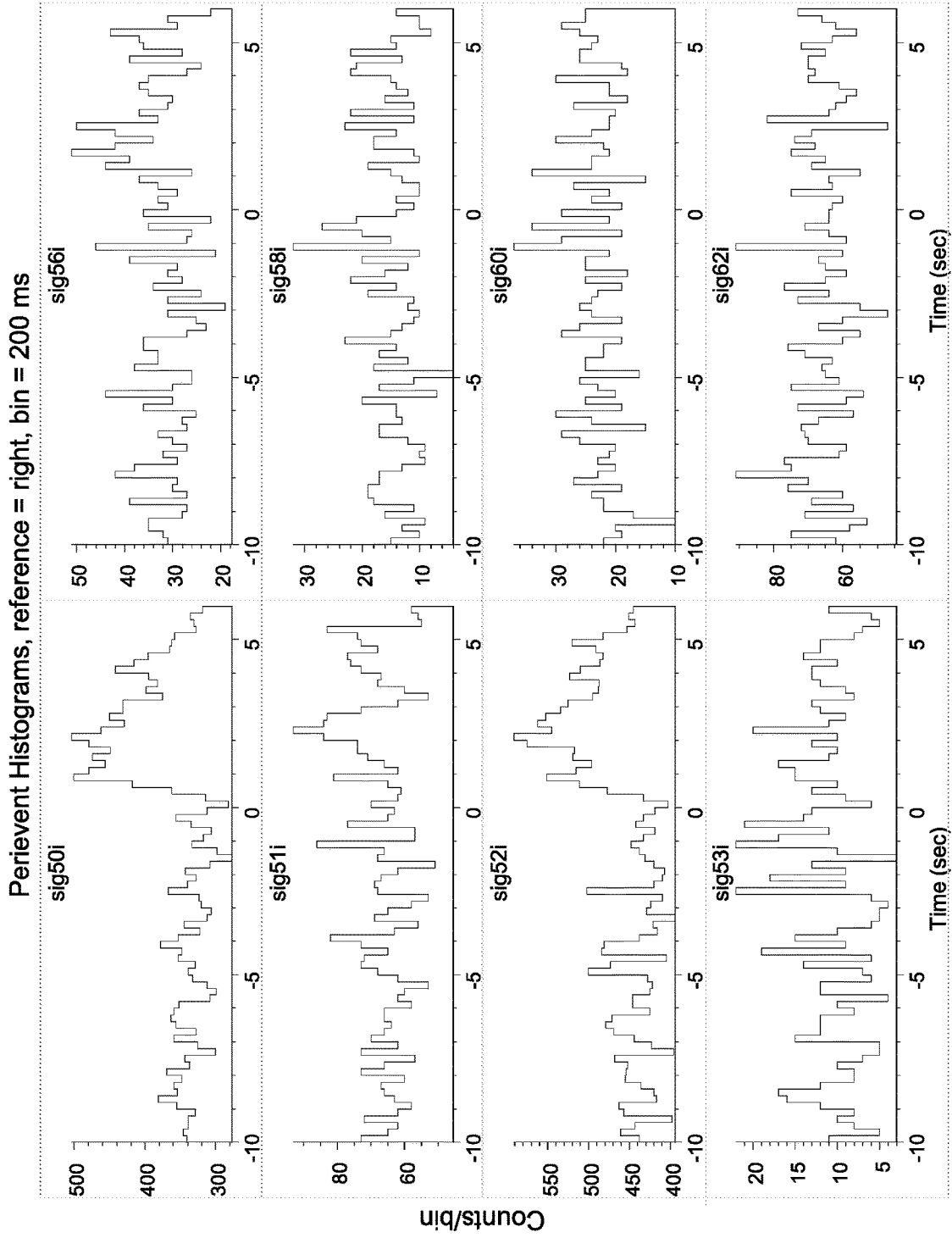
Figure 3 B) ND1

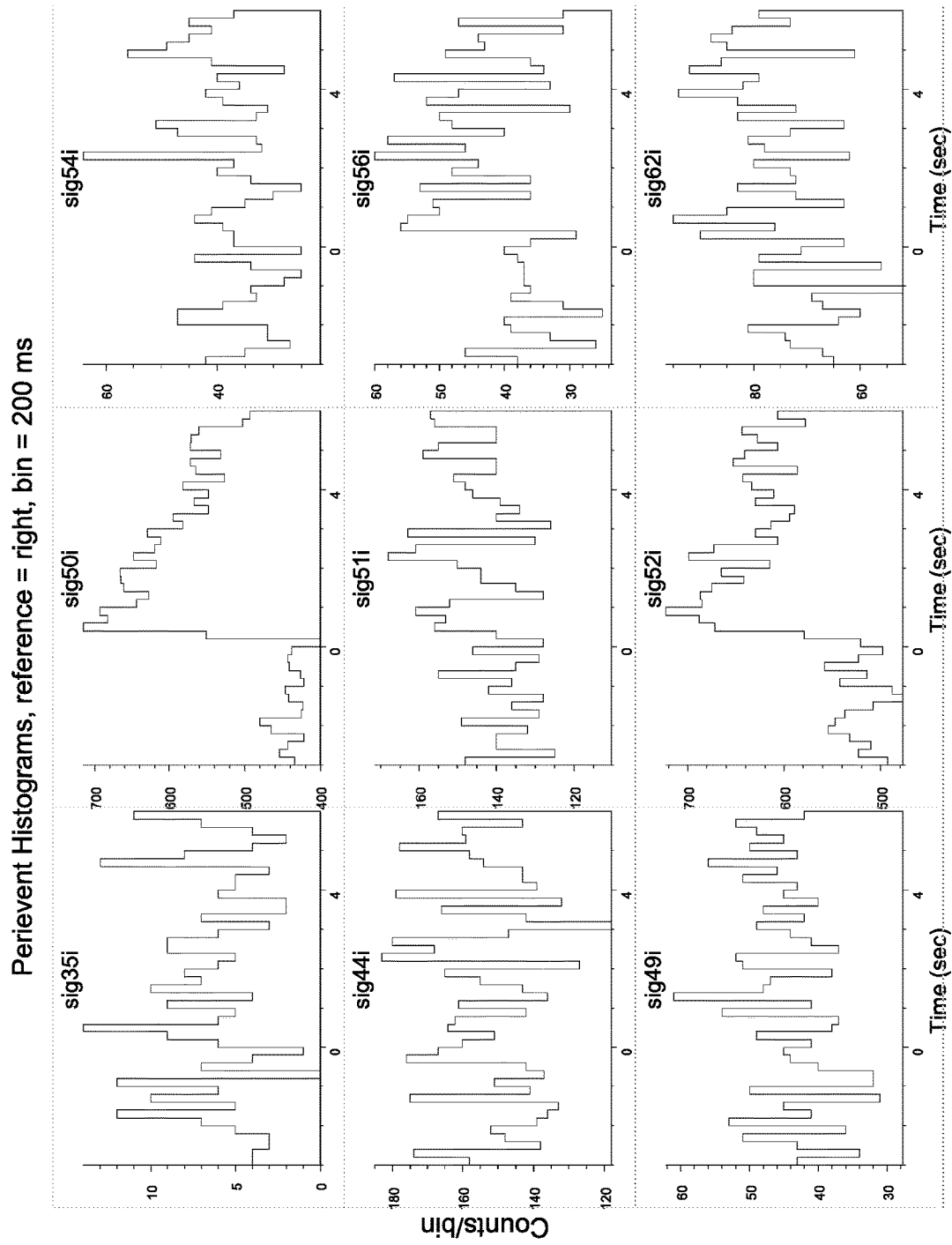
Figure 3 C) ND0

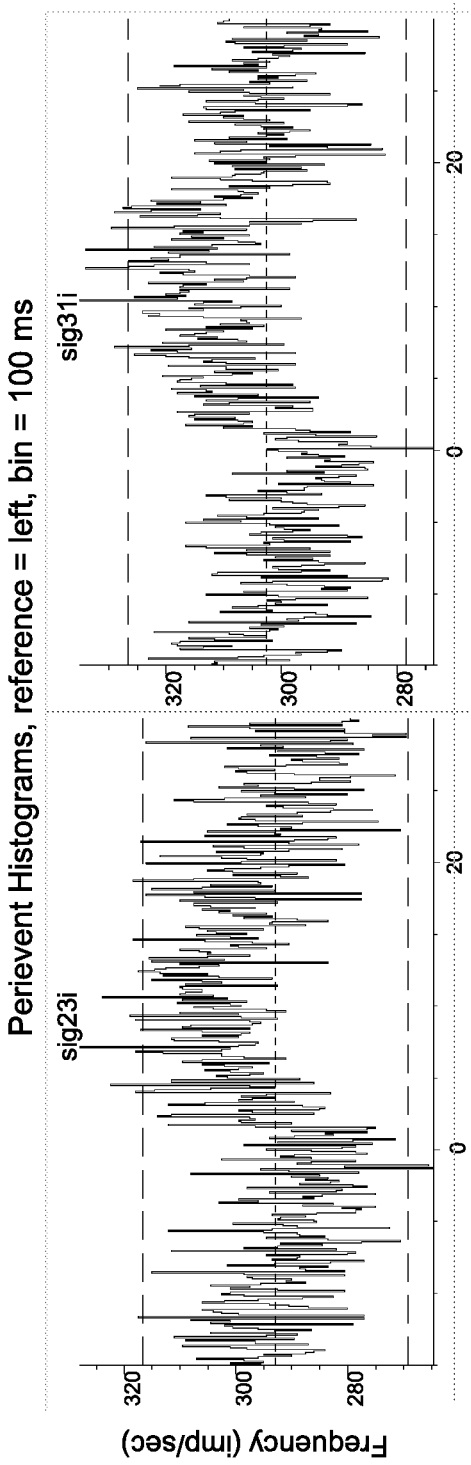
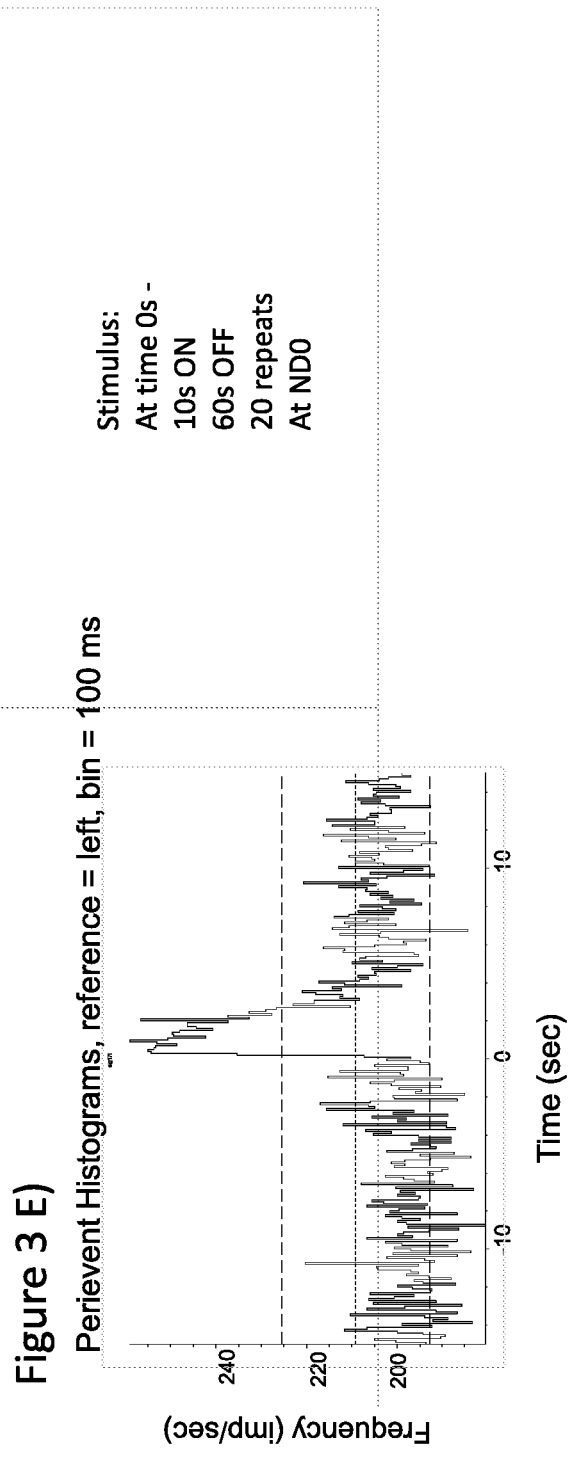
Figure 3 D)
Figure 3 E)

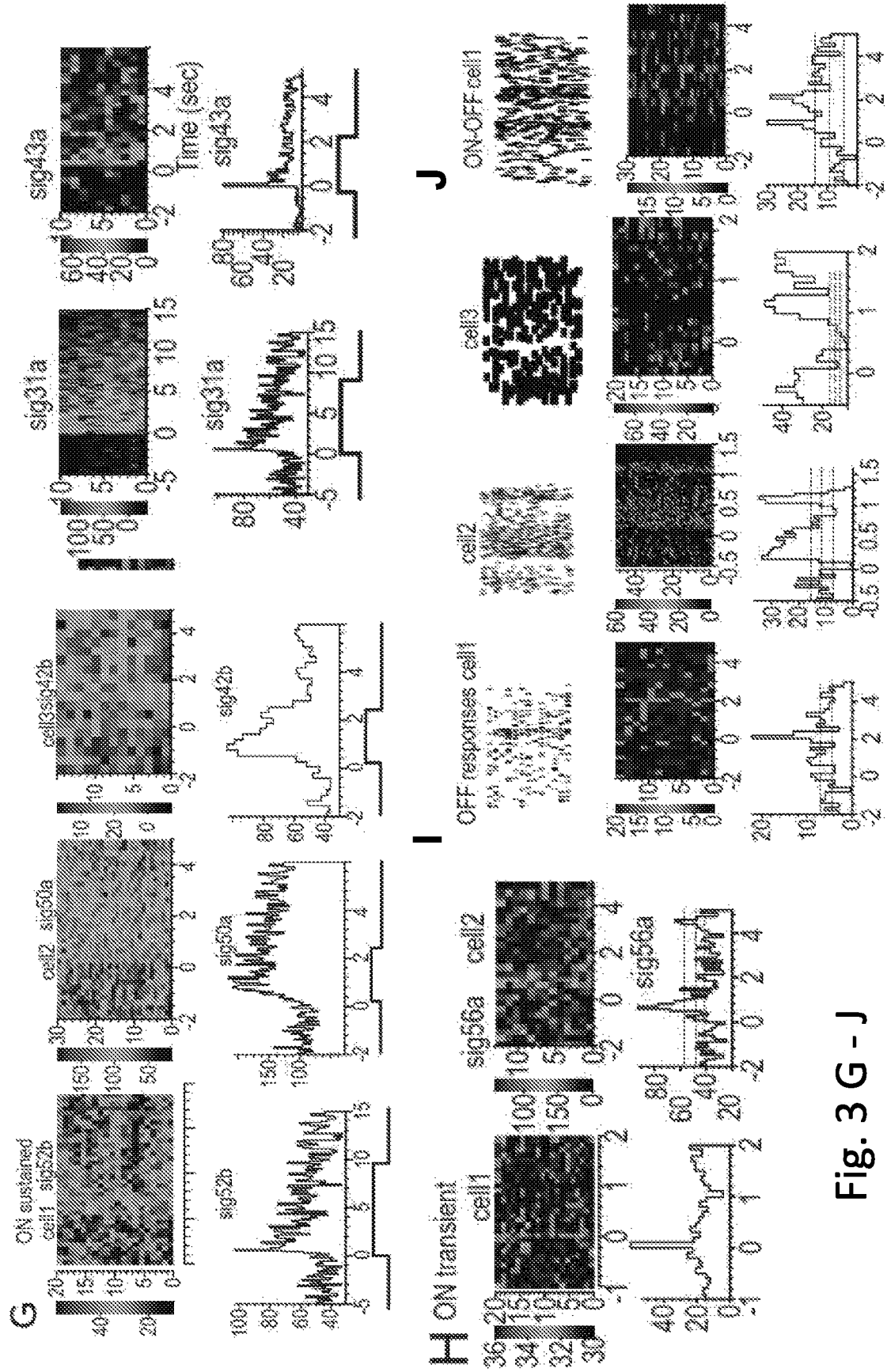
Fig. 3 G - J

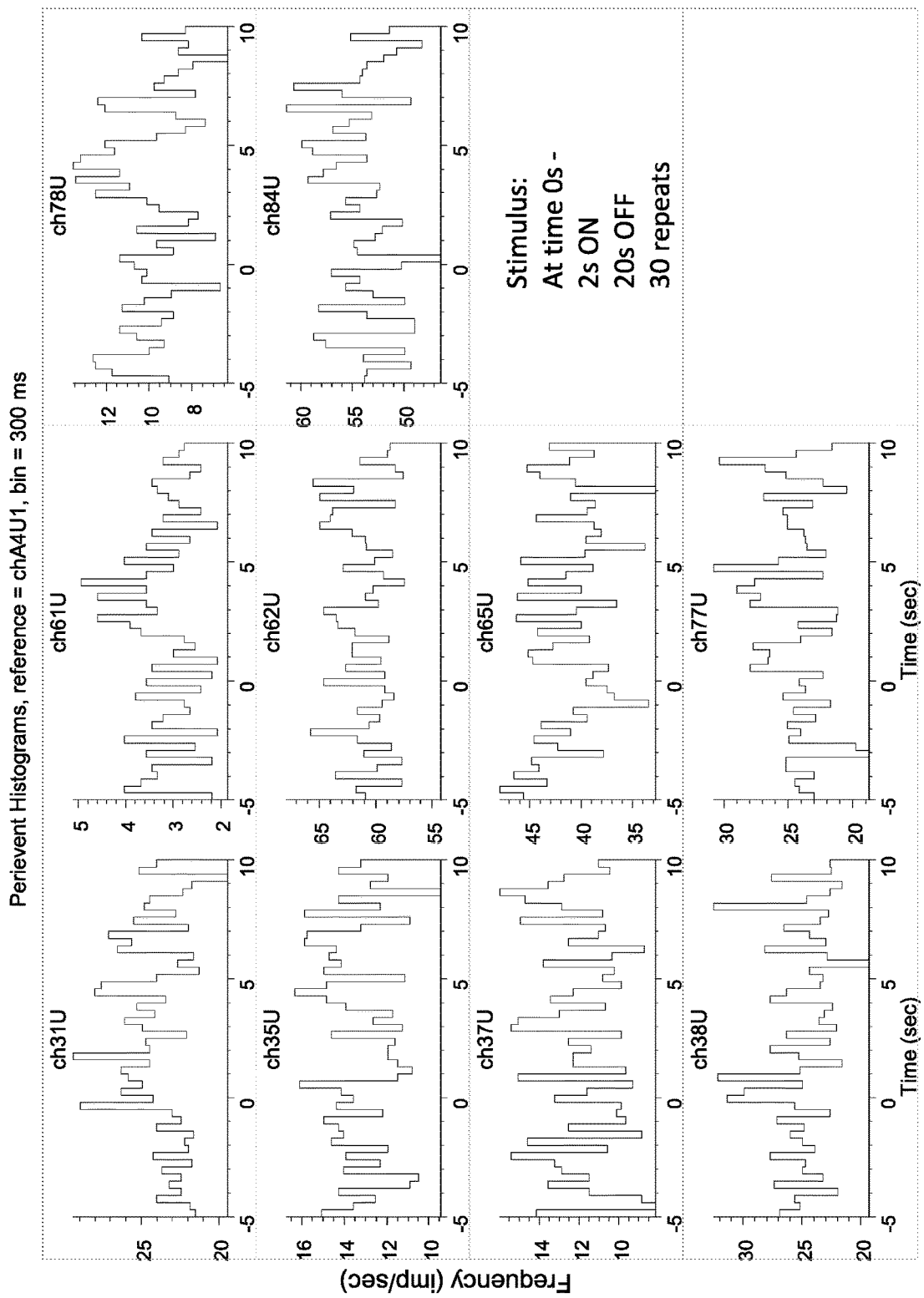
Figure 4 A) ND2

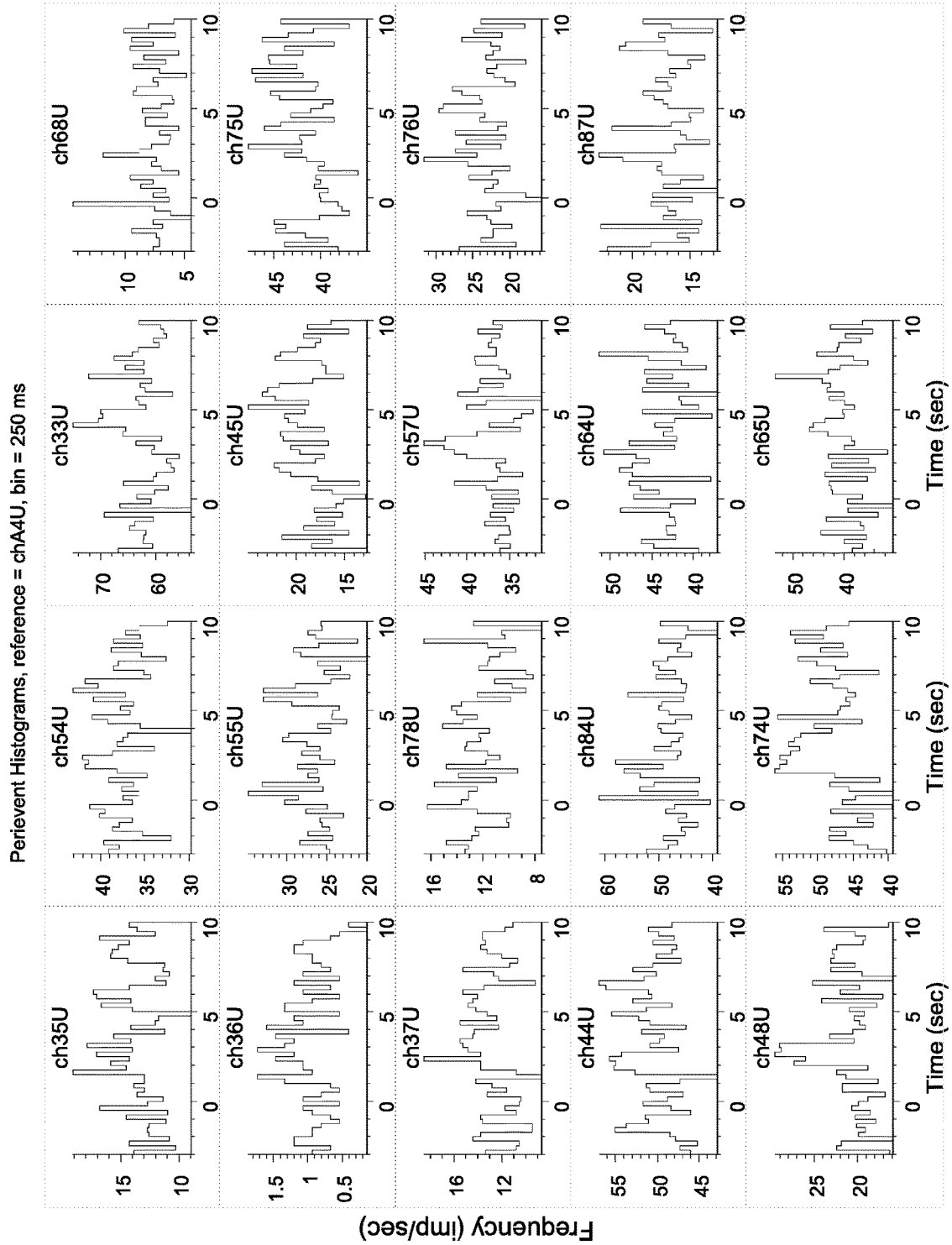
Figure 4 B) ND1

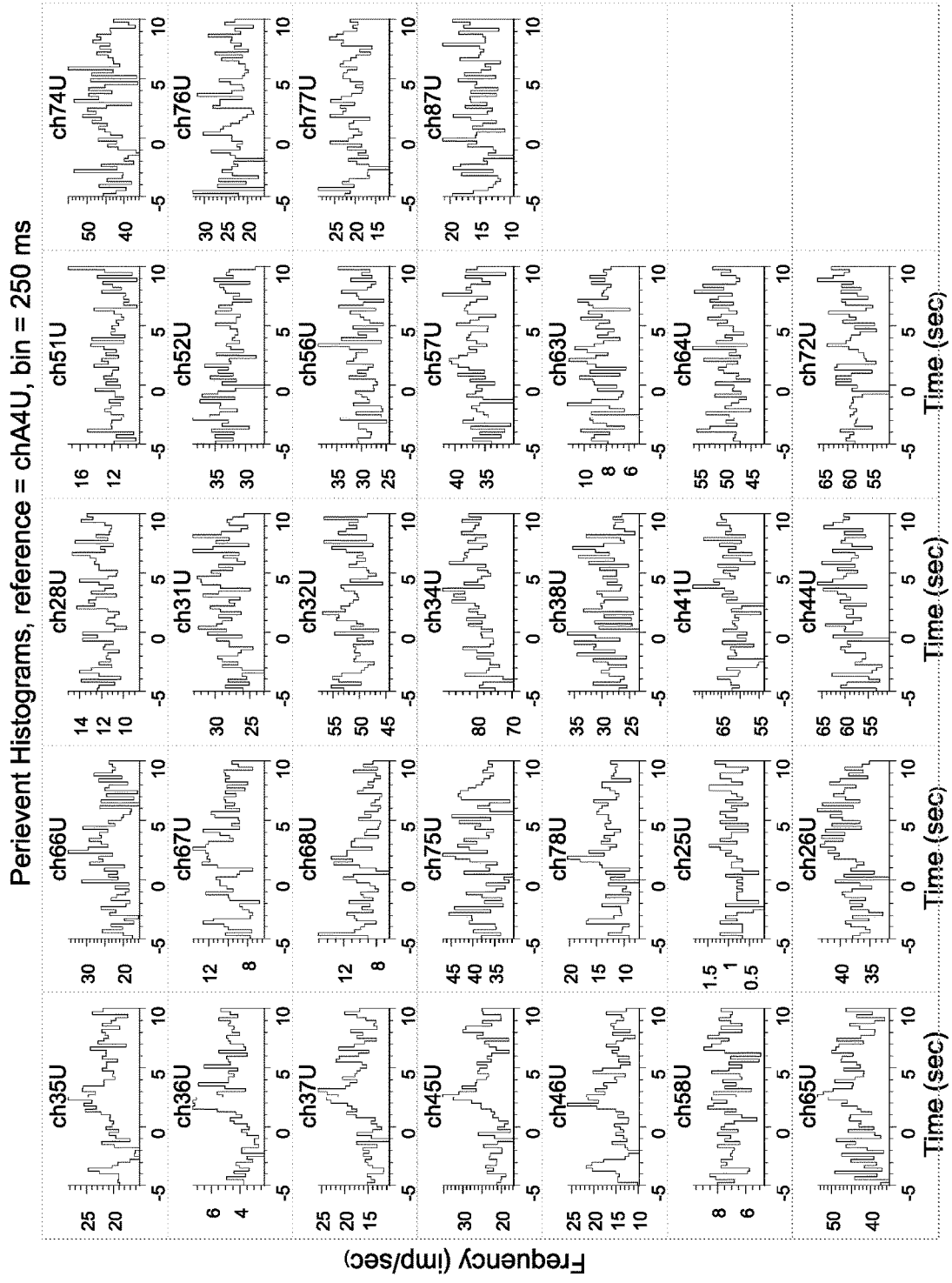
Figure 4 C) ND0

Light responses at ND2

Time (s)

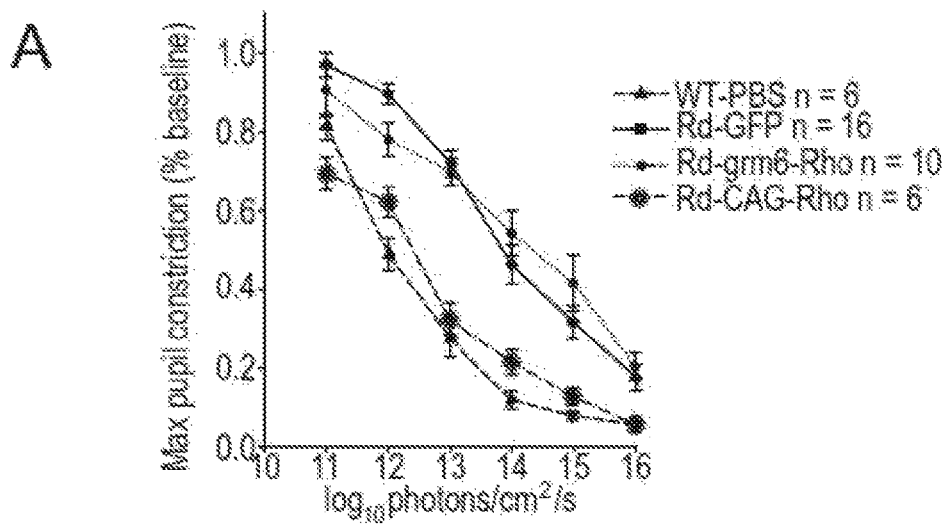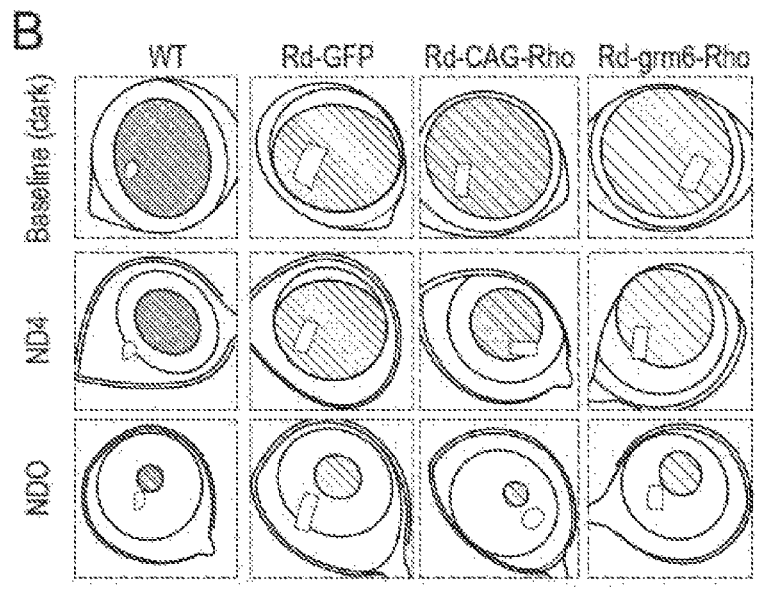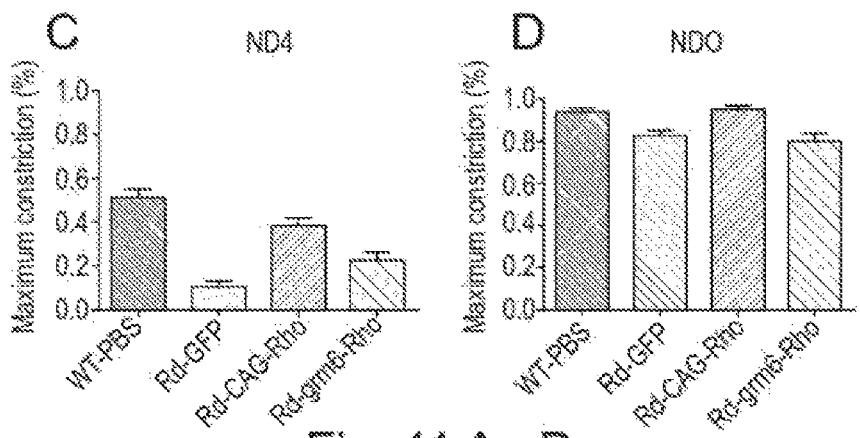
Fig. 11 A - D

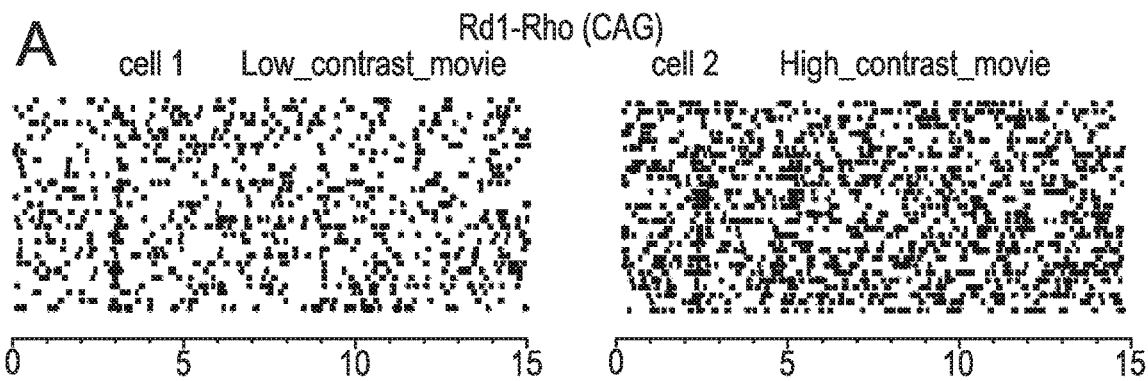
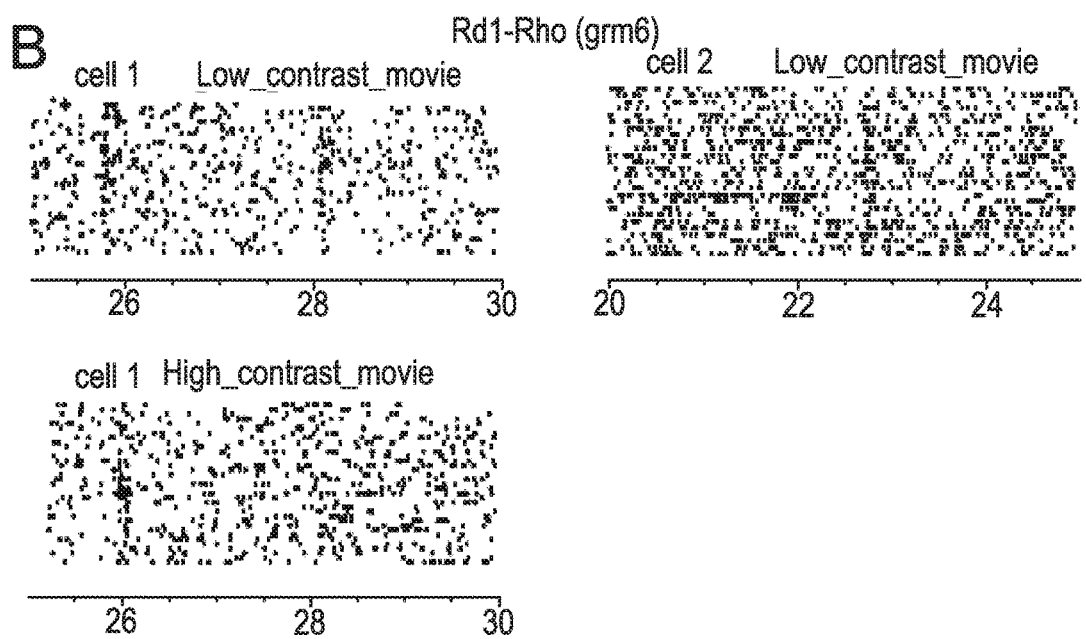
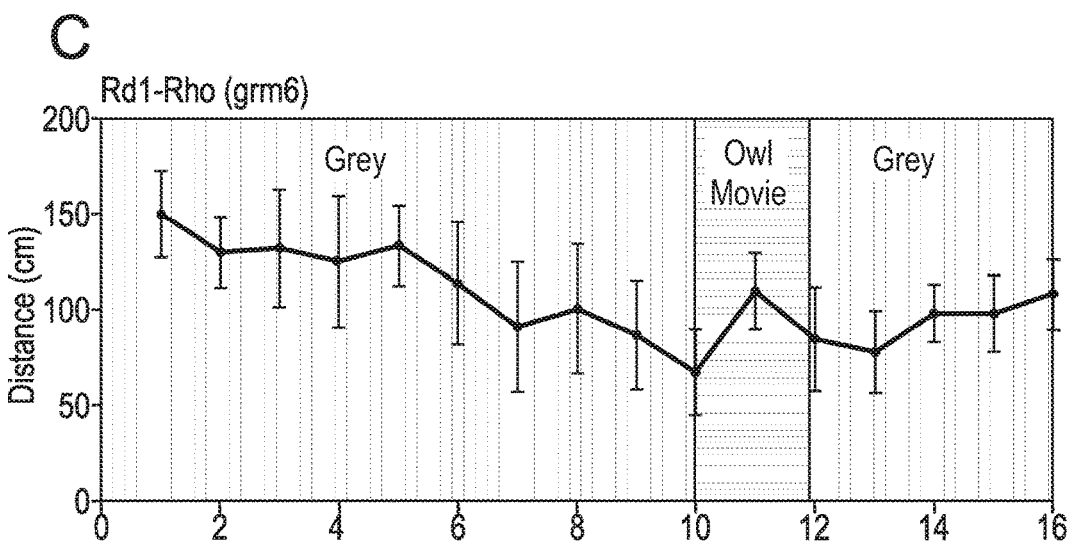
Fig. 16 A-C

TREATMENT OF RETINAL DEGENERATION USING GENE THERAPY

CROSS-REFERENCE TO RELATED APPLICATIONS

This application is a National Phase of International Application No. PCT/GB2015/050516 filed Feb. 24, 2015, currently pending, which designated the U.S. and that International Application was published under PCT Article 21(2) in English. Both applications also include a claim of priority under 35 U.S.C. § 119(a) and § 365(b) to British patent application No. GB 1403260.1 filed Feb. 25, 2014, the entirety of which is hereby incorporated by reference.

FIELD OF THE INVENTION

The present invention relates to an improved method of providing photoreceptor function to a cell, for example for use in the treatment of retinal degeneration. The present invention also relates to compositions and kits, in particular for use in such methods.

BACKGROUND

The retina of the vertebrate eye serves the same function as a film in a camera, receiving a visual image created by light passing through the lens and cornea of the eye. The image received is translated into chemical and electrical signals which are transmitted to the brain via the optic nerve.

The retina is a complex structure, comprising ten distinct layers of different cell types. Of these layers, it is the photoreceptor layer which is responsible for translating the incoming light into a chemical and/or electrical signal which can be read by the brain and interpreted into an image. The photoreceptor layer comprises photosensitive cells of two types, known as rod cells and cone cells. These cell types are both responsible for reacting to incoming light and producing an electrical signal, but differ in in their positioning within the retina and the type of light which they react to. Specifically, rod cells function mostly in dim light and are found predominantly in the peripheral retina. Cone cells are more reactive to bright light (i.e. daytime vision) are responsible for colour vision and are found at highest density in the central retina. The retina also contains a third less numerous type of photoreceptor cell—photosensitive ganglion cells—which are responsible for measuring background light, but not image processing.

The rod and cone cells of the photoreceptor layer of the retina are able to react to light and convert it to an electrical signal due to the presence of photosensitive pigments (referred to as photopigments) therein, which undergo a chemical change when the cell is exposed to light. These photopigments are G-protein-coupled receptors. The photopigments comprise a protein moiety which is coupled to a chromophoric cofactor known as retinal. Exposure to light causes an isomerisation of the retinal cofactor from a cis-retinal to a trans-retinal, which in turn causes a conformational change in the opsin protein, known as photobleaching. This is the first step in a signaling cascade which results in a signal being transmitted along the optic nerve. In order to retain photosensitivity, opsins thus need a continuous supply of cis retinal. Neither rod nor cone photoreceptor cells are able to produce cis-retinal themselves. The major source of cis-retinal in the retina is the RPE (retinal pigment epithelium) which takes all trans-retinal from bleached opsin and produces cis-retinal. In the intact retina, rod and cone cells abut the RPE allowing them access to this regenerated chromophore.

In humans, several closely related photopigments exist, known as the opsin family. In humans, these comprise 3 cone opsins which are sensitive to different wavelengths (the origin of colour vision), rhodopsin found in rod cells, and melanopsin found in ganglion cell photoreceptors. The cone opsins include LWS opsin for yellowish-green, MWS opsin for green, and SWS opsin for bluish-violet. These opsins show high sequence identity.

Conditions such as retinal dystrophies cause blindness due to destruction of the photoreceptors in the outer retina (i.e. the rods and cones). These conditions may be a result of direct damage to the photoreceptors, or photoreceptors being indirectly destroyed as a result of pathology in the retinal pigment epithelium and/or choroid. Severe visual impairment is common in advanced stages of the degeneration. These conditions are currently incurable. Retinal dystrophies can be divided into rod-cone dystrophies (also called retinitis pigmentosa), cone-rod dystrophies and macular dystrophies. In rod-cone dystrophies the rod photoreceptors degenerate resulting in a loss of peripheral vision and night vision, and frequently this is followed by cone destruction leading to a loss of central and colour vision. Conversely in the cone-rod dystrophies there is initially a loss of cone photoreceptors leading to a loss of detailed and colour vision and this is then followed by rod degeneration resulting in a loss of peripheral vision and night blindness. Both forms can result in blindness with extensive or complete loss of visual field. Another type of retinal dystrophy called macular dystrophy results in a loss of central vision, but peripheral vision is preserved.

However, despite the loss of outer retinal photoreceptors, inner retinal neurons, including bipolar cells and retinal ganglion cells, can survive and retain their ability to send visual information to the brain. These neurons therefore, provide a promising niche for emerging optogenetic therapies that aim to convert them into directly visual photoreceptors and recreate the photosensitivity that has been lost with the degeneration. Several therapeutic strategies have shown promising results in attempts to replace or revive these inner retinal neurons and restore vision. Transplantation of photoreceptor cells, or their progenitor lines, is a major approach under pre-clinical study and has been shown to restore vision to blind mice at late stage of degeneration after complete loss of photoreceptors. In attempts to revive inner retinal neurons, implantable electronic prostheses have triggered retinal ganglion cell (RGC) firing through external cameras and have provided crude spatial discrimination for at least some patients (Zrenner E, et al. 2011, Proc Biol Sci 278(1711):1489-1497; Humayun M S, et al. 2012, Ophthalmology 119, 779-788). Another strategy uses microbial opsins as photoswitches of neuronal activity and they have been used to elicit light-evoked activity in degenerate retinas. To this extent it has been shown that intravitreal injection of an AAV-2 vector carrying the channelrhodopsin-2 gene (ChR2) in the rd1 mouse leads to light activated depolarization or 'ON' responses in RGCs and visually evoked potentials in the cortex. This study led by Bi et al. (Bi A, et al 2006, Neuron. 2006; 6; 50(1):23-33.)) provided the first proof-of-principle that retinal function can be restored using optogenetics. (Lagali P S, et al 2008, Nat Neurosci. 2008 June; 11(6):667-75; Cronin T, et al 2014, EMBO Mol Med. 2014 Aug. 4; 6(9):1175-90; Macé E et al 2014, Mol Ther. 2015 January; 23(1):7-16) as well as cone photoreceptors (Busskamp V, et al 2010, Science. 2010 Jul. 23;

329(5990):413-7.) have been successfully converted to artificial light-sensors leading to partial rescue of visual function in blind mice. In addition, recently developed synthetic photoswitches have shown promising results in rescuing vision in blind mice. The 'one-component' azobenzene-based photoswitches use small molecules, AAQ or DENAQ (Polosukhina A, et al 2012, Neuron. 2012 Jul. 26; 75(2): 271-82; Tochitsky I, et al 2014, Neuron. 2014 Feb. 19; 81(4):800-13.) that directly photosensitise native ion channels of neurons. The 'two-component' photoswitches, LiGluR/MAG, (Caporale N, et al 2011, Mol Ther. 2011 July; 19(7):1212-9; Gaub B M, et al 2014, Proc Natl Acad Sci USA. 2014 Dec. 23; 111(51):E5574-83) first genetically express synthetically engineered light-gated ionotropic glutamate receptor (LiGluR) in retinas and then require addition of a photoswitch molecule (MAG) for activation. Both systems have shown to impart light sensitivity to blind mouse and canine (Gaub B M, et al 2014, Proc Natl Acad Sci USA. 2014 Dec. 23; 111(51):E5574-83) retinas and restore basic visual functions in rodents.

However improvements are still necessary in the treatment of these conditions.

The present invention aims to overcome or ameliorate the problems associated with the treatment of retinal degeneration.

BRIEF SUMMARY OF THE INVENTION

Thus, in a first aspect of the present invention, there is provided a method of providing photoreceptor function to a cell, the method comprising introducing into the vitreal cavity of an eye i) a nucleic acid sequence encoding a photosensitive protein; and ii) an extracellular matrix degradation enzyme.

In a second aspect of the present invention, there is provided a composition comprising i) a nucleic acid sequence encoding a photosensitive protein and ii) an extracellular matrix degradation enzyme. Preferably, the composition is therapeutic.

In a third aspect of the present invention, there is provided i) a nucleic acid sequence encoding a photosensitive protein; and ii) an extracellular matrix degradation enzyme, for use in a method of providing photoreceptor function to a cell.

In a fourth aspect of the invention, there is provided a method of providing photoreceptor function to a cell, the method comprising introducing into an eye a nucleic acid vector comprising a nucleic acid encoding a human photoreceptor protein. In this aspect, preferably the vector is introduced without administration of an extracellular matrix degradation enzyme (for example, it is introduced without co-administration of an enzyme, wherein co-administration includes separate, sequential or combined administration during the same therapy). The method may further comprise expressing the vector in inner retinal cells, wherein expression of the human photoreceptor protein renders an inner retinal cell photoreceptive.

In a fifth aspect of the invention, there is provided a nucleic acid vector comprising a nucleic acid encoding a human photoreceptor protein.

DESCRIPTION OF THE DRAWINGS

Embodiments of the invention are further described hereinafter with reference to the accompanying drawings, in which:

FIG. 4 shows data from in-vitro MEA recordings;

FIG. 11 shows ectopic expression of rod opsin restores visual behaviour in treated blind rd1 mice: A) Irradiance-response curves for maximum pupillary constriction during 10 s of white light at a range of light intensities (A). Rod opsin treated rd1 eyes (untargeted CAG expression, red) show a marked improvement in visual sensitivity compared to GFP injected rd1 eyes (green). With targeted expression (Grm6, blue) the pupillary light reflex remained largely impaired. Data for wild-type mice injected with PBS/enzyme mixture are shown for comparison (black). Data are normalised to pupil size immediately preceding the onset of light. Values are mean±SEM, with n indicating the number of animals examined; B) Representative infrared images of pupil area measured in the dark (baseline), at ND4 (11.8 log photons/cm2/s) and at ND0 (15.8 log photons/cm2/s) for WT, Rd1-GFP, Rd1-CAG-hRho, Rd1-grm6-hRho mice; C, D) Mean maximum pupillary constriction across the population of all four groups of mice at ND4 (11.8 log photons/cm2/s; C) and ND0 (15.8 log photons/cm2/s; D). Number of animals examined: WT n=6; Rd1-GFP n=16; Rd1-CAG-hRho n=10; Rd1-grm6-hRho n=6. Error bars are SEM.

FIG. 16 shows targeted rod opsin expression restores responses to naturalistic movie scenes: A, B) Raster plots for representative responsive dLGN units from Rd1-CAG-hRho (A) and Rd1-Grm6-hRho (B) mice exposed to multiple presentations of a 30 s naturalistic movie (mice moving in an open arena in horizontal view); C) Open box activity plots from grey screen light (shagged in grey) to a looming owl movie (shaded in green) for Rd1-grm6-hRho (n=5). Data are population mean of distance travelled in a preceding 30-second bin ±SEM;

DETAILED DESCRIPTION OF THE INVENTION

Figure 1:
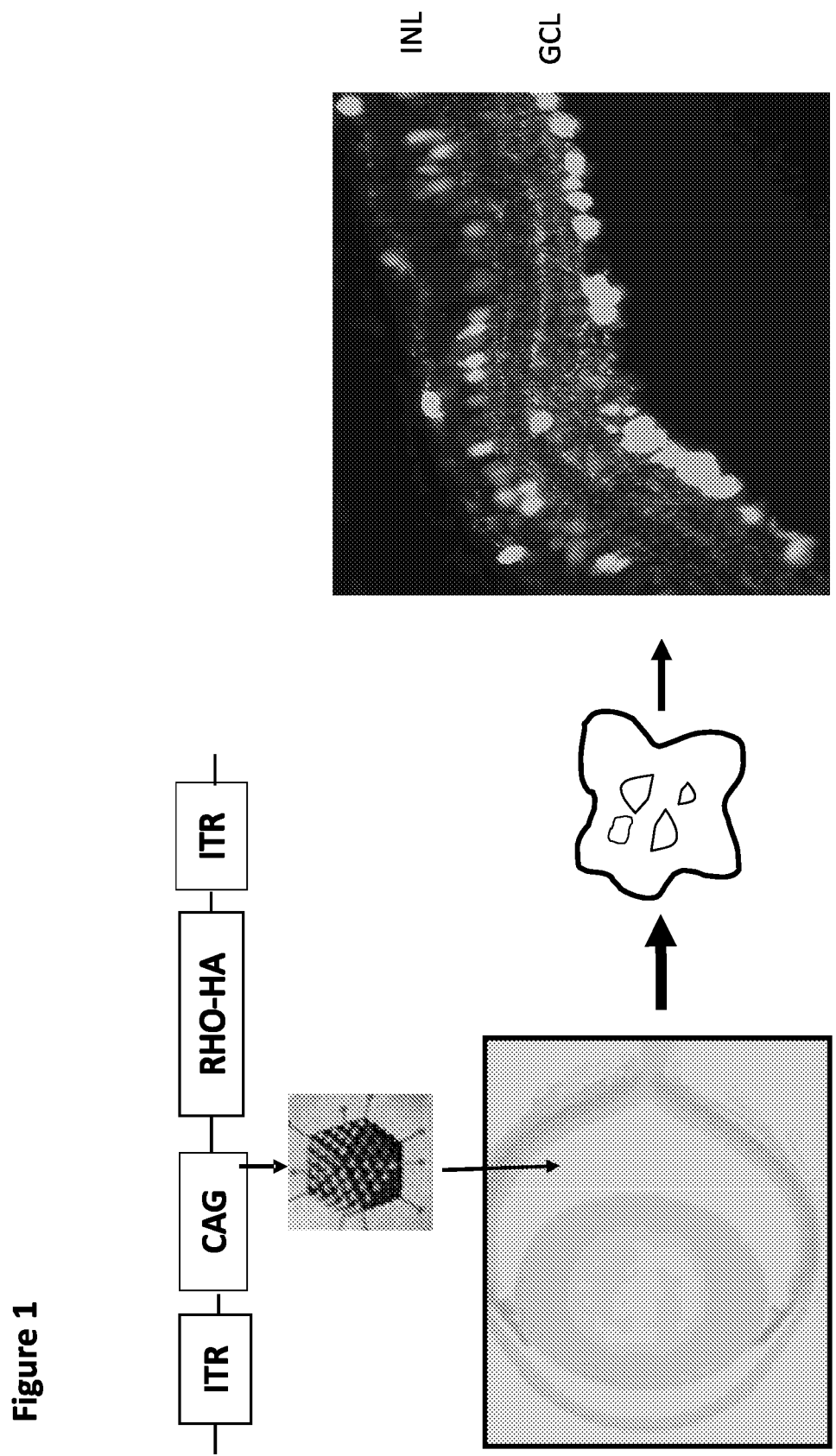
FIG. 1 shows intraocular injections and gene delivery via AAV.

The present invention relates to the use of a human photoreceptor protein to provide photoreceptor function to a cell, in order to restore photosensitivity in degenerated or partially degenerated retinas. Such native photoreceptor function is lost with photoreceptor degeneration. The present invention is based upon the surprising finding that expression of a human photoreceptor protein in the inner retina can provide photoreceptor function to the inner retinal neurone cells. The transgenic expression of a human photoreceptor protein in the inner retina has the advantage of minimising potential immunogenic adverse effects, in contrast to the use of microbial opsins and electronic arrays respectively. In addition, outside photoreceptors, this GPCR has potential to hijack cell's machinery and provide a completely self-contained photoreceptive mechanism, capable of supporting light detection on its own and without any further interventions, unlike synthetic photoswitches that require constant exogenous supply of a photoswitch for activation. Moreover, rod opsin requires visible light for activation, and through the native GPCR amplification cascade it has a potential to function under low light intensities in contrast to current channel based or synthetic photoswitch systems, which are unable to amplify signals at the protein level.

Intravitreal injection as a method for gene therapy has particular advantages in terms of being less technically challenging in access to the retina, and reduced risk of complications during administration, in particular where retinas have become thin through degradation.

The present invention is, in part, based upon the discovery that co-administration of an extracellular matrix degradation enzyme in gene therapy leads to increased transduction of retinal cells, thus improving the outcome in terms of increased restoration of vision. The invention represents an improvement over previous intra-vitreal gene therapy methods, by enabling increased transduction by reducing barriers to contact of the foreign genetic material with the target cells.

The combined application of gene therapy and an extracellular matrix degradation enzyme has led to surprising results in particular where the gene therapy comprises introduction of a nucleic acid sequence encoding rhodopsin to the vitreous of an eye. Rhodopsin requires the all-trans retinal that is produced following visual transduction to be transported to the retinal pigment epithelium (RPE) for it to be converted into all-cis retinal which is then transported back to the rod cells for further visual response. This recycling has been thought to be dependent upon the intimate contact between rod cells and the RPE. Inner retinal cells, even in the presence of retinal dystrophies where the rods and cones degenerate, would not be physically associated with the RPE in the same way. The present inventors have unexpectedly observed that providing rhodopsin to inner retinal cells by gene therapy produces a visual response, despite lack of contact between the functioning inner retinal cells and the RPE. Furthermore, it is thought that the inner retinal cells do not have the intracellular machinery required to work in conjunction with rhodopsin to produce an electrical signal that could then be transmitted via the ganglion cells to the brain.

The results are further surprising because rhodopsin works by hyperpolarising cells in response to light (the brains equivalent of switching the cells "off"), where it might be assumed that vision would require inner retinal cells to be depolarised (switched "on") by light.

The present invention provides for the administration of an extracellular matrix degradation enzyme in combination with a nucleic acid sequence encoding a photosensitive protein to restore photosensitive function to the retina. The retina and vitreous comprise a variety of extracellular matrix molecules, including proteoglycans (with different classes of glycosaminoglycan (GAG) chains) such as heparan sulphate proteoglycans (HSPGs), chondroitin sulphate proteoglycans (CSPGs), and dermatan sulphate proteoglycans (DSPGs); hyaluronan, collagens such as type IV collagen in the inner limiting lamina; laminins; nidogen 1 and 2, and a variety of other proteins and glycoproteins which are known to persons skilled in the art.

It is envisaged that the present invention may utilise any enzyme which is capable of degrading an extracellular matrix protein or carbohydrate (such as glycosaminoglycan) present in the vitreous and/or in the retina and/or internal limiting membrane, and/or retinal extracellular matrix. In particular, an enzyme for use in the present invention may be one which is capable of degrading an extracellular matrix protein or carbohydrate which is provided in the retina, or an extracellular matrix protein or carbohydrate which is provided in the path between the vitreous and the cells of the retina and which may therefore impact upon transduction of a nucleic acid sequence. Preferred are enzymes which degrade glycosaminoglycans (GAGs).

An extracellular matrix degradation protein may be selected from the group consisting of a collagenase, hyaluronan lyase, heparinase I, heparinase II, heparinase III, chondroitin ABC lyase, chondroitin AC lyase, a metalloproteinase, an ADAMTS, a plasmin (serine protease plasmin or its truncated form microplasmin (Ocriplasmin)), neutrophil elastase and cathepsin G, neuraminidase, N-glycanase, O-glycanase, and pronase. A particularly preferred enzyme may be selected from the group consisting of Hyaluronan lyase from *Streptomyces hyalurolyticus* (EC 4.2.2.1; contained within Genbank accession CP003990); Hyaluronidase from bovine testes (EC 3.2.1.35); chondroitin ABC lyase from *Proteus vulgaris* (EC 4.2.2.4) and heparinase III from *Flavobacterium heparinum* (EC 4.2.2.8; Genbank accession L12534, preferably version L12534.1). Enzymes for use in the present invention are available from commercial sources, for example Sigma Aldritch.

By "degrade" or "degradation enzyme" means an enzyme which is capable of breaking down a protein or carbohydrate. A protein can be broken into peptide sequences or amino acids, for example by hydrolysis of the peptide bond. A carbohydrate may be broken down into oligosaccharides or single sugar units. A protein and/or carbohydrate may be fully or partially degraded, meaning that a portion of it may be broken down into smaller fragments, whereas the remainder of the protein and/or carbohydrate may be in its native form. Preferably, a degraded extracellular matrix protein or carbohydrate loses some ability to provide structural and/or biochemical support to a cell, such that a nucleic acid sequence introduced into the vitreous can better access a retinal cell. In particular, a degraded extracellular matrix protein loses some or all its ability to impede movement of a nucleic acid sequence (e.g. gene delivery vector, such as a viral vector), within the vitreous, and into and across the retina. Any loss in extracellular matrix function is sufficiently minimal so that it does not have any significant adverse effect on the eye or vision.

Herein, reference to an extracellular matrix degradation enzyme includes active fragments thereof. An active fragment may be a portion or shorter version of the native enzyme, which retains the ability to function as an extracellular matrix degradation enzyme i.e. it retains the ability to degrade an extracellular matrix protein or carbohydrate, as defined herein. An active fragment may comprise 70%, 75%, 80%, 85%, 90%, 95%, 96%, 97%, 98%, or 99% of the sequence of the native enzyme.

Herein, reference to an enzyme includes one or more enzymes. Thus, the invention provides for the co-administration of a single enzyme or a combination of two or more enzymes. Preferably, where two or more enzymes are provided, they are each selected from the group defined above. Where two or more enzymes are administered, they may be provided in separately, sequentially, or two or more may be provided in combination. Preferably, two enzymes are administered in combination. Where two or more separate doses of enzyme are provided, any one or more of these may be provided in combination with the nucleic acid sequence.

An enzyme for use in the present invention may be derived from any suitable source. The source may be mammalian or non-mammalian. It may be derived from an animal, plant, bacterial, or archeabacterial source. Where mammalian, it is preferred that it is a human enzyme. It may be isolated or purified from such a source. It may be produced as a recombinant protein. Alternatively, it may be synthetically produced.

The nucleic acid and amino acid sequences of enzymes for use in the present invention are known in the art.

Herein, enzymes include fragments and derivatives of native enzymes. Preferably a fragment or derivative shares at least 70%, 75%, 80%, 85% or 90%, at least 91, 92, 93, 94, 95, 96, 97, 98, or at least 99% sequence identity with a native enzyme, over a length of 50%, 60%, 70%, 80%, 90%, or at least 95% of the length of a native enzyme.

Sequence identity is determined by comparing the two aligned sequences over a predetermined comparison window (which may be 50%, 60%, 70%, 80%, 90%, 95%, or 100% of the length of the reference nucleotide sequence or protein), and determining the number of positions at which identical residues occur. Typically, this is expressed as a percentage. The measurement of sequence identity of a nucleotide sequences is a method well known to those skilled in the art, using computer implemented mathematical algorithms such as ALIGN (Version 2.0), GAP, BESTFIT, BLAST (Altschul et al J. Mol. Biol. 215: 403 (1990)), FASTA and TFASTA (Wisconsin Genetic Software Package Version 8, available from Genetics Computer Group, Accelrys Inc. San Diego, Calif.), and CLUSTAL (Higgins et al, Gene 73: 237-244 (1998)), using default parameters.

An enzyme for use in the present invention may be provided in dry form, which includes either dehydrated or lyophilised forms. Typically, an enzyme will be provided in lyophilised form. Alternatively, an enzyme may be provided as an aqueous solution, for example pre-dissolved in water at a predetermined concentration and volume. For administration, an aqueous form is preferred, although it is envisaged that a product or kit of the invention may suit the provision of a dried form of the enzyme, optionally with instructions for dissolving. Thus, a method of the invention may comprise using a dried enzyme to produce an enzyme solution. Preferably, this is achieved by dissolving or reconstituting the enzyme in an aqueous or non-aqueous solvent. Suitable solvents are those which are non-toxic, and suitable for use with humans or animals. Preferably, a suitable solvent is sterile. An example of a suitable solvent is sterile phosphate buffered saline. Methods for dissolving dried proteins are known in the art.

The present invention provides for the administration of a nucleic acid sequence encoding a photosensitive protein to the retina, in order to restore photoreceptive ability to the retina. A photosensitive protein is one which reacts to light, by undergoing a chemical or physical change. By photoreceptive, means a cell which is photosensitive or comprises a photosensitive protein. The terms photoreceptive or photoreceptor and photosensitive may be used interchangeably.

A nucleic acid sequence for use in the invention may encode any photosensitive protein. Preferably, the nucleic acid sequence of the invention encodes a mammalian or non-mammalian photosensitive protein. It may be mammalian, non-mammalian, plant, bacterial, or archeabacterial in origin. Where mammalian, it is preferred that it encodes a human protein. A nucleic acid sequence for use in the present invention may be selected from the group consisting of rhodopsin, melanopsin, a cone opsin (in particular LWS opsin, MW opsin, and SWS opsin), neuropsin (Opn5), encaphalopsin (Opn3), a parapineal opsin, VAopsin, parapinopsin; parietopsin, pinopsin, TMT opsin, Jelly fish opsin, C-opsin, cryptochrome, and any invertebrate retinal opsins and/or opsins normally supporting extra-retinal photosensitivity in animals.

A nucleic acid sequence for use in the present invention may be selected depending upon the subject to be treated, such that the nucleic acid sequence encodes a photosensitive protein which is native to the retina of the subject to be treated. Thus, for example, where the subject is a human, a nucleic acid sequence will preferably encode a human photosensitive protein, for example rhodopsin. However, it is envisaged that in certain embodiments, a nucleic acid sequence may be provided which encodes a photosensitive protein which is not native to the subject to be treated, but which preferably does not raise an immune response in the subject.

The nucleic acid sequences and amino acid sequences of many photosensitive proteins are known in the art. For example, the nucleic acid sequences of preferred photosensitive proteins are provided as follows:
Melanopsin: *Homo sapiens* opsin 4 (OPN4), mRNA (cDNA clone MGC:142118 IMAGE:8322610), GenBank: BC113558, Version BC113558.1;
Rhodopsin: *Homo sapiens* rhodopsin (RHO), GenBank: BC111451.3, Accession NM_000539, Version NM_000539.3 GI:169808383;
Cone *homo sapiens* opsin 1: *Homo sapiens* opsin 1, long-wave sensitive, OPN1LW-NCBI Reference Sequence: Accession: NM_020061, Version NM_020061.5;
*Homo sapiens* opsin 1, medium-wave sensitive OPN1MW-NM_000513, version NM_000513.2;
*Homo sapiens* opsin 1 short-wave-sensitive (OPN1SW) NM_001708, version NM_001708.2.
Parapinopsin (Genbank Accession NM_001200073, Version NM_001200073.1 GI:318056020);
Parietopsin (Genbank Accession DQ100320, Version DQ100320.1 GI:73666459); Pinopsin (Genbank Accession AF487546, Version AF487546.1 GI:20805654);
VA opsin (Genbank Accession AF233520, Version AF233520.1 GI:8272567);
TMT opsin (Genbank Accessions AH011520 AF349943 AF349944 AF349945, version AH011520.2 GI:339511123);
Jelly fish opsin (Genbank Accession AB435549, Version AB435549.1 GI:210049957);
OPN3 (Genbank Accession NM_014322, Version NM_014322.2 GI:71999130);
OPN5 (Genbank Accession AY377391, Version AY377391.1 GI:38482095); C-opsin (Genbank Accession HF566407, version HF566407.1 GI:543581059); and Cryptochrome (Genbank Accession NM_169852, Version NM_169852.1 GI:24648151).

In the fourth or fifth aspects of the invention described above, the photoreceptor protein is a human photoreceptor protein. A human photoreceptor protein may be human Rhodopsin (also referred to as Rh1, OPN2, RHO) or a photopsin. A photospin may be selected from the group consisting of Long Wavelength Sensitive (OPN1LW) Opsin, Middle Wavelength Sensitive (OPN1MW) Opsin and Short Wavelength Sensitive (OPN1SW) Opsin.

Long Wavelength Sensitive (OPN1LW) Opsin has a $\lambda_{max}$ of 560 nm, in the yellow-green region of the electromagnetic spectrum. It is also referred to as "red opsin", "L opsin" or "LWS opsin". Middle Wavelength Sensitive (OPN1MW) Opsin has a $\lambda_{max}$ of 530 nm, in the green region of the electromagnetic spectrum. It is also referred to as the "green opsin", "M opsin" or "MWS opsin". Short Wavelength Sensitive (OPN1SW) Opsin has a $\lambda_{max}$ of 430 nm, in the blue region of the electromagnetic spectrum. It is also referred to as the "blue opsin", "S opsin" or "SWS opsin".

The nucleic acid sequence encoding a human photoreceptor protein may be the *Homo sapiens* rhodopsin (RHO) gene (GenBank: BC111451.3, Accession NM_000539, Version NM_000539.3 GI:169808383), or a fragment or derivative thereof.

The nucleic acid sequence encoding a human photoreceptor protein may be the Cone *homo sapiens* opsin 1, long wave sensitive OPN1LW (NCBI Reference Sequence: Accession: NM_020061, Version NM_020061.5), or a fragment or derivative thereof.

The nucleic acid sequence encoding a human photoreceptor protein may be the Cone *homo sapiens* opsin 1: medium-wave sensitive OPN1MW, (NCBI Reference Sequence: Accession: NM_000513.2; (Science 232 (4747), 193-202 (1986)), or a fragment or derivative thereof.

The nucleic acid sequence encoding a human photoreceptor protein may be the Cone *homo sapiens* opsin 1: short-wave-sensitive (OPN1SW) NM_001708, version NM_001708.2, or a fragment or derivative thereof.

Reference to a nucleic acid sequence encoding a photosensitive protein includes nucleic acid sequences which are derivatives of the sequences described herein, or encode a shorter version, or a fragment of a photosensitive protein, wherein the derivative or fragment retains substantially the same photosensitive function as the native photosensitive protein. By substantially the same is meant at least 70%, 75%, 80%, 85%, 90%, 95%, 96%, 97%, 98%, or 99% of the photosensitive function of the native protein. A fragment may comprise 70%, 75%, 80%, 85%, 90%, 95%, 96%, 97%, 98%, or 99% of the sequence of the native protein.

Preferably a fragment or derivative of a nucleic acid sequence shares at least 70%, 75%, 80%, 85% or 90%, at least 91, 92, 93, 94, 95, 96, 97, 98, or at least 99% sequence identity with a reference nucleic acid sequence, over a length of 50%, 60%, 70%, 80%, 90%, or at least 95% of the length of a reference nucleic acid sequence. A derivative is preferably active, and may include substitutions and/or deletions and/or additions compared to the native sequence. Derivatives may also include portions of other gene sequences, which provide a desired activity or function to the photosensitive protein.

Sequence identity is determined by comparing the two aligned sequences over a predetermined comparison window (which may be 50%, 60%, 70%, 80%, 90%, 95%, or 100% of the length of the reference nucleotide sequence or protein), and determining the number of positions at which identical residues occur. Typically, this is expressed as a percentage. The measurement of sequence identity of a nucleotide sequences is a method well known to those skilled in the art, using computer implemented mathematical algorithms such as ALIGN (Version 2.0), GAP, BESTFIT, BLAST (Altschul et al J. Mol. Biol. 215: 403 (1990)), FASTA and TFASTA (Wisconsin Genetic Software Package Version 8, available from Genetics Computer Group, Accelrys Inc. San Diego, Calif.), and CLUSTAL (Higgins et al, Gene 73: 237-244 (1998)), using default parameters.

A nucleic acid sequence may be a DNA, RNA, cDNA, or PNA. It may be genomic, recombinant or synthetic. A nucleic acid sequence may be isolated or purified. It may be single stranded or double stranded. Preferably, a nucleic acid sequence will encode a photosensitive protein, as described herein. A nucleic acid sequence may be derived by cloning, for example using standard molecular cloning techniques including restriction digestion, ligation, gel electrophoresis, for example as described in Sambrook et al; Molecular Cloning: A laboratory manual, Cold Spring Harbour laboratory Press). A nucleic acid sequence may be isolated, for example using PCR technology. Such technology may employ primers based upon the sequence of the nucleic acid sequence to be amplified. By isolated is meant that the nucleic acid sequence is separated from any impurities and from other nucleic acid sequences and/or proteins which are naturally found associated with the nucleic acid sequence in its source. Therefore, it may be separated from flanking nucleic acid sequences, or from chromosomal material or sequence. Preferably, it will also be free of cellular material, culture medium, or other chemicals from a purification/production process. A nucleic acid sequence may be synthetic, for example produced by direct chemical synthesis e.g. using the phosphotriester method (Narang et al Meth Enzymol 68: 109-151 1979). A nucleic acid sequence may be provided as naked nucleic acid, or may be provided complexed with a protein or lipid.

The sequence may be altered to improve expression efficiency (for example by truncating C-terminus or introducing targeting motifs), or to alter characteristics of the light response (for example by removing or adding residues targeted by rhodopsin kinases as part of the signal termination process).

With the sequence information provided, the skilled person can use available cloning techniques to produce a nucleic acid sequence or vector suitable for transduction into a cell.

Preferably, a nucleic acid sequence encoding a photosensitive protein is provided as a vector, preferably an expression vector. Preferably, it may be provided as a gene therapy vector, preferably which is suitable for transduction and expression in a target retinal cell. A vector may be viral or non-viral (e.g. a plasmid). Viral vectors include those derived from adenovirus, adenoassociated virus (AAV) including mutated forms, retrovirus, lentivirus, herpes virus, vaccinia virus, MMLV, GaLV, Simian Immune Deficiency Virus (SIV), HIV, pox virus, and SV40. A viral vector is preferably replication defective, although it is envisaged that it may be replication deficient, replication competent or conditional. A viral vector may typically persist in an extrachromosomal state without integrating into the genome of the target retinal cell. A preferred viral vector for introduction of a nucleic acid sequence encoding a photosensitive protein to a retinal target cell is an AAV vector, for example self-complementary adenoassociated virus (scAAV). Selective targeting may be achieved using a specific AAV serotype (AAV serotype 2 to AAV serotype 12) or a modified version of any of these serotypes including AAV 4YF and AAV 7m8 vectors. In aspects of the invention where the vector is provided by intra-vitreous administration, the vector may be one which has been modified such that it does not bind to one or more proteins of the ECM. For example, a preferred vector may comprise a modified heparin sulphate binding site, such that it has reduced or an inability to bind heperan sulphate, such as AAV 7m8 (Dalkara D et al Sci Transl Med 2013; 5:189ra76).

A viral vector may be modified to delete any non-essential sequences. For example, in AAV the virus may be modified to delete all or part of IX gene, E1a and/or E1b gene. For wild type AAV, replication is at extremely low efficiency, without the presence of helper virus, such as adenovirus. For recombinant adeno-associated virus, preferably the replication and capsid genes are provided in trans (in pRep/Cap plasmid), and only the 2 ITRs of AAV genome are left and packaged into a virion, while the adenovirus genes required are provided either provided by adenovirus or another plasmid. Similar modifications may be made to a lentiviral vector.

A viral vector has the ability to enter a cell. However, a non-viral vector such as plasmid may be complexed with an agent to facilitate its uptake by a target cell. Such agents include polycationic agents. Alternatively, a delivery system such as a liposome based delivery system may be used.

A vector for use in the present invention is preferably suitable for use in vivo or in vitro, and is preferably suitable for use in a human.

A vector will preferably comprise one or more regulatory sequences to direct expression of the nucleic acid sequence in a target retinal cell. A regulatory sequence may include a promoter operably linked to the nucleic acid sequence, an enhancer, a transcription termination signal, a polyadenylation sequence, an origin of replication, a nucleic acid restriction site, and a homologous recombination site. A vector may also include a selectable marker, for example to determine expression of the vector in a growth system (for example a bacterial cell) or in a target retinal cell.

By "operably linked" means that the nucleic acid sequence is functionally associated with the sequence to which it is operably linked, such that they are linked in a manner such that they affect the expression or function of one another. For example, a nucleic acid sequence operably linked to a promoter will have an expression pattern influenced by the promoter.

A promoter mediates expression of the nucleic acid sequence to which it is linked. A promoter may be constitutive or may be inducible. A promoter may direct ubiquitous expression in the inner retinal cells, or neurone specific expression. In the latter case, a promoter may direct cell type specific expression, for example to ON bipolar or OFF bipolar cells. Suitable promoters will be known to persons skilled in the art. For example, a suitable promoter may be selected from the group consisting of L7, thy-1, recoverin, calbindin, human CMV, GAD-67, chicken beta-actin, hSyn, Grm6, Grm6 enhancer-SV40 fusion protein. Targeting may be achieved using cell specific promoters, for example e.g. Grm6-SV40 for selective targeting of ON-bipolar cells. The Grm6 promoter is a fusion of 200-base pair enhancer sequence of the Grm6 gene encoding for ON-bipolar cell specific metabotropic glutamate receptor, mGluR6, and an SV40 eukaryotic promoter. Preferred sources of the Grm6 gene are mouse and human. Ubiquitous expression may be achieved using a pan-neuronal promoter, examples of which are known and available in the art. One such example is CAG. The CAG promoter is a fusion of CMV early enhancer and chicken β-actin promoter.

The present invention provides a therapeutic composition comprising i) a nucleic acid sequence encoding a photosensitive protein and ii) an extracellular matrix degradation enzyme. A composition may be provided in a pharmaceutically acceptable excipient.

The present invention also provides a nucleic acid vector comprising a nucleic acid encoding a human photoreceptor protein. The human photoreceptor protein may be human Rhodopsin (also referred to as Rh1, OPN2, RHO) or a photopsin. A photospin may be selected from the group consisting of Long Wavelength Sensitive (OPN1LW) Opsin, Middle Wavelength Sensitive (OPN1MW) Opsin and Short Wavelength Sensitive (OPN1SW) Opsin. The vector may be provided as a composition, for administration to a subject.

A composition may be a liquid or a solid, for example a powder, gel, or paste. Preferably, a composition is a liquid, preferably an injectable liquid. Suitable excipients will be known to persons skilled in the art.

In the fourth and fifth aspects of the invention relating to the administration of a nucleic acid vector comprising a nucleic acid encoding a human photoreceptor protein, the vector may be administered to an eye by sub-retinal or intra-vitreous administration. In either mode of administration, the vector is preferably provided as an injectable liquid. Preferably, the injectable liquid is provided as a capsule or syringe. In this aspect, preferably the nucleic acid is introduced without administration of an extracellular matrix degradation enzyme (i.e. it is introduced without co-administration of an enzyme, wherein co-administration includes separate, sequential or combined administration during the same therapy) as defined herein. In this aspect, preferably the injectable liquid does not comprise an extracellular matrix degradation enzyme In aspects of the invention comprising administration of an extracellular matrix degradation enzyme, an enzyme may be provided separately or in combination with the nucleic acid sequence, i.e. as a single composition. Where provided separately, the enzyme and nucleic acid sequence may be provided in the same excipient or in different excipients. In such an embodiment, the may be held separately, for example in separate microcapsules. Thus, in a preferred embodiment, the present invention provides a composition comprising i) a first injectable liquid comprising a nucleic acid sequence encoding a photosensitive protein; and ii) a second injectable liquid comprising an extracellular matrix degradation enzyme. Preferably, the first and second injectable liquids are provided in separate containers, such as capsules or syringes, preferably within the same packaging.

Preferably, a composition of the first, second and third aspects of the invention is provided for separate, sequential or combined administration of the nucleic acid and enzyme to a subject A composition of the invention may be provided for use in a method of providing photoreceptor function to a cell. In an embodiment, a composition of the invention may be provided for use in a method of restoring photoreceptor function of a retina. In an embodiment, a composition of the invention may be provided for use in a method of restoring vision to a subject. In an embodiment, a composition of the invention may be provided for use in a method of treating a retinal degenerative condition, for example a retinal dystrophy including a rod dystrophy, a rod-cone dystrophy, a cone-rod dystrophy, a cone dystrophy and a macular dystrophy; other forms of retinal or macular degeneration, an ischaemic condition, uveitis and any other disease resulting from loss of photoreceptor ability, e.g retinal pigmentosa.

The present invention provides a kit comprising a nucleic acid vector comprising a nucleic acid encoding a human photoreceptor protein. The human photoreceptor protein may be as described above. The nucleic acid vector may be provided as a composition, as described herein. The composition may be an injectable liquid. In this aspect, preferably the kit does not comprise an extracellular matrix degradation enzyme.

The present invention provide a kit comprising i) a nucleic acid sequence encoding a photosensitive protein; and ii) an extracellular matrix degradation enzyme. In a kit of the invention, the extracellular matrix degradation enzyme and nucleic acid sequence may be provided separately, or in combination. They may each, independently, be provided as a composition, for example as described herein. Thus, a kit of the invention may comprise i) a nucleic acid sequence encoding a photosensitive protein and ii) an extracellular matrix degradation enzyme, wherein the nucleic acid sequence and/or the enzyme are provided as a composition. The nucleic acid sequence and enzyme may be provided in combination, in a single composition, or may be provided as separate compositions. Where provided separately, the enzyme and nucleic acid sequence may be provided in the same excipient or in different excipients. In such an embodiment, the may be held separately, for example in separate microcapsules.

In a preferred embodiment, a kit may comprise i) a first injectable liquid comprising a nucleic acid sequence encoding a photosensitive protein and ii) a second injectable liquid comprising an extracellular matrix degradation enzyme. Preferably, the first and second injectable liquids are provided in separate containers, such as capsules or syringes, preferably within the same packaging.

A kit of the invention may further comprise instructions for use, a dosage regimen, one or more fine needles, one or more syringes, and solvent.

A kit of the invention may be provided for use in a method of providing photoreceptor function to a cell. In an embodiment, a kit of the invention may be provided for use in a method of restoring photoreceptor function of a retina. In an embodiment, a kit of the invention may be provided for use in a method of restoring vision to a subject. In an embodiment, a kit of the invention may be provided for use in a method of treating a retinal degenerative condition, for example a retinal dystrophy including a rod dystrophy, a rod-cone dystrophy, a cone-rod dystrophy, a cone dystrophy and a macular dystrophy; other forms of retinal or macular degeneration, an ischaemic condition, uveitis and any other disease resulting from loss of photoreceptor ability.

The present invention provides a method of providing photoreceptor function to a cell, the method comprising introducing into an eye a nucleic acid vector comprising a nucleic acid encoding a human photoreceptor protein. The human photoreceptor protein may be as described above. The method may comprise sub-retinal or intra-vitreous administration of the nucleic acid vector to the inner retinal cells of the eye. In this aspect, preferably the method does not comprise administration of an extracellular matrix degradation enzyme. The present invention provides a nucleic acid vector comprising a nucleic acid encoding a human photoreceptor protein for use in a method of treating retinal degeneration by providing photoreceptor function to a cell. In this aspect, preferably an extracellular matrix degradation enzyme is not used (i.e. the nucleic acid is introduced without co-administration of an enzyme, wherein co-administration includes separate, sequential or combined administration during the same therapy).

The present invention provides a method of providing photoreceptor function to a cell, the method comprising introducing into the vitreal cavity of an eye i) a nucleic acid sequence encoding a photosensitive protein and ii) an extracellular matrix degradation enzyme. The present invention provides i) a nucleic acid sequence encoding a photosensitive protein and ii) an extracellular matrix degradation enzyme for use in a method of providing photoreceptor function to a cell.

The present invention also provides a method of augmenting photoreceptor function in a retina, in particular following rod and/or cone cell degeneration, the method comprising introducing into the vitreal cavity of an eye a nucleic acid vector comprising a nucleic acid encoding a human photoreceptor protein. The human photoreceptor protein may be as described above. The method may comprise sub-retinal or intra-vitreous administration of the nucleic acid vector to the inner retinal cells of the eye. In this aspect, preferably the method does not comprise administration of an extracellular matrix degradation enzyme. The present invention provides a nucleic acid nucleic acid vector comprising a nucleic acid encoding a human photoreceptor protein for use in treating retinal degeneration by augmenting photoreceptor function in a retina. The human photoreceptor protein may be as described above. In this aspect, preferably an extracellular matrix degradation enzyme is not used (i.e. the nucleic acid is introduced without co-administration of an enzyme, wherein co-administration includes separate, sequential or combined administration during the same therapy).

The present invention also provides a method of augmenting photoreceptor function in a retina, in particular following rod and/or cone cell degeneration, the method comprising providing photoreceptor function to a cell as described herein. The present invention provides i) a nucleic acid sequence encoding a photosensitive protein and ii) an extracellular matrix degradation enzyme for use in a method of augmenting photoreceptor function in a retina, in particular following rod and/or cone cell degeneration, wherein the method comprises providing photoreceptor function to a cell as described herein.

The present invention also provides a method of restoring vision to a subject, the method comprising introducing into an eye a nucleic acid vector comprising a nucleic acid encoding a human photoreceptor protein. The human photoreceptor protein may be as described above. The method may comprise sub-retinal or intra-vitreous administration of the nucleic acid vector to the inner retinal cells of the eye. In this aspect, preferably the method does not comprise administration of an extracellular matrix degradation enzyme. The present invention provides a nucleic acid nucleic acid vector comprising a nucleic acid encoding a human photoreceptor protein for use in restoring vision to a subject. The human photoreceptor protein may be as described above. In this aspect, preferably an extracellular matrix degradation enzyme is not used (i.e. the nucleic acid is introduced without co-administration of an enzyme, wherein co-administration includes separate, sequential or combined administration during the same therapy).

The present invention also provides a method of restoring vision to a subject, the method comprising providing photoreceptor function to a cell as described herein. The present invention provides i) a nucleic acid sequence encoding a photosensitive protein and ii) an extracellular matrix degradation enzyme for use in a method of restoring vision to a subject, wherein the method comprises providing photoreceptor function to a cell as described herein.

The present invention also provides a method of treating retinal disease a subject, the method comprising introducing into an eye a nucleic acid vector comprising a nucleic acid encoding a human photoreceptor protein. The human photoreceptor protein may be as described above. The method may comprise sub-retinal or intra-vitreous administration of the nucleic acid vector to the inner retinal cells of the eye. In this aspect, preferably the method does not comprise administration of an extracellular matrix degradation enzyme. The present invention provides a nucleic acid vector comprising a nucleic acid encoding a human photoreceptor protein for use in treating retinal disease in a subject. The human photoreceptor protein may be as described above. In this aspect, preferably an extracellular matrix degradation enzyme is not used (i.e. the nucleic acid is introduced without co-administration of an enzyme, wherein co-administration includes separate, sequential or combined administration during the same therapy). The disease may be a retinal dystrophy including a rod dystrophy, a rod-cone dystrophy, a cone-rod dystrophy, a cone dystrophy and a macular dystrophy; other forms of retinal or macular degeneration, an ischaemic condition, uveitis and any other disease resulting from loss of photoreceptor ability.

The present invention also provides a method of treating a retinal degenerative disease, the method comprising providing photoreceptor function to a cell as described herein. Thus, the present invention provides i) a nucleic acid sequence encoding a photosensitive protein and ii) an extracellular matrix degradation enzyme for use in a method of treatment of a disease, as defined herein. The disease may be a retinal dystrophy including a rod dystrophy, a rod-cone dystrophy, a cone-rod dystrophy, a cone dystrophy and a macular dystrophy; other forms of retinal or macular degeneration, an ischaemic condition, uveitis and any other disease resulting from loss of photoreceptor ability.

By providing photoreceptor function to a cell means that a cell which previously did not have photoreceptor ability or whose photoreceptor ability has degenerated, wholly or partially, becomes photo-receptive upon expression therein of the foreign nucleic acid sequence encoding a photosensitive protein. Such a cell may be referred to herein as a transformed cell, because it comprises therein non-native nucleic acid. Preferably, a transformed retinal cell exhibits some or all of the photoreceptor ability of a native photoreceptive cell. Preferably, a transformed cell exhibits at least the same or substantially the same photoreceptive ability of a native retinal photoreceptor cell. Preferably, a transformed cell exhibits higher photoreceptive ability than a diseased or degenerating native retinal photoreceptor cell. Therefore, a transformed cell will preferably have increased photoreceptor compared to a degenerated or diseased cell from the same source, maintained under the same conditions, without treatment. A transformed cell can be distinguished from a native cell by the presence therein of exogenous nucleic acid.

By augmenting photoreceptor function is meant increasing photoreceptor function of the retina, either by increasing the function in photoreceptor cells such as rod or cone cells, and/or by providing photoreceptor function to a cell. Thus, the retina will have an increased ability to receive light signals and transmit such signals compared to a retina which has not been treated with method as described herein. The increase may be by any amount, preferably to wild type levels.

By restoring vision in a subject is meant that the subject shows improved vision compared to prior to treatment, for example using vision tests as described herein. Restoring includes any degree in improvement, including full restoration of vision to perfect or near perfect vision.

By treating disease is meant administration of as nucleic acid and extracellular degradation enzyme as described herein to ameliorate or alleviate of one or more symptoms of a disease selected from the group consisting of a retinal dystrophy including a rod dystrophy, a rod-cone dystrophy, a cone-rod dystrophy, a cone dystrophy and a macular dystrophy; another forms of retinal or macular degeneration, an ischaemic conditions, uveitis and any other disease resulting from loss of photoreceptor ability. Amelioration or alleviation may result in an improvement of peripheral or central vision, and/or day or night vision.

Methods of the invention comprise introducing into the vitreal cavity of an eye a nucleic acid sequence encoding a photosensitive protein. Preferably, the method comprises contacting a cell with a nucleic acid sequence encoding a photosensitive protein. Preferably, a cell is a retinal cell, preferably an ON-bipolar cell, an OFF-bipolar cell, a horizontal cell, a ganglion cell and/or an amacrine cell.

Preferably, a method of the invention comprises targeting a nucleic acid sequence encoding a photosensitive protein to the retina of an eye, preferably to a non-photoreceptive cell of the retina, preferably to an ON-bipolar cell, an OFF-bipolar cell, a horizontal cell, a ganglion cell and/or an amacrine cell. Thus, by contacting a cell includes transfection and/or transduction of a cell.

Where an enzyme is administered, the enzyme does not need to be internalised into a retinal cell, but may remain in the vitreal cavity or in the retina, where it degrades extracellular matrix proteins to improve access of the nucleic acid sequence to the retinal cells.

A method of the invention is preferably performed in vivo.

The nucleic acid sequence encoding a photosensitive protein and an enzyme may be provided separately or sequentially or in combination. Where provided simultaneously (i.e. in combination), a nucleic acid sequence and an enzyme may be provided as a single composition which is introduced into the vitreal cavity, or may be provided as separate compositions but provided to the vitreal cavity simultaneously. If provided separately, a nucleic acid sequence and enzyme may be provided in separate compositions, and may be provided either at the same time, or sequentially. When provided sequentially, an enzyme may be provided before or after a nucleic acid sequence, preferably before. In the fourth and fifth aspects, an enzyme is not con-administered by the methods described above.

Where two or more enzymes are provided, they may be introduced in a combined single dose or in multiple doses. An enzyme dose may be provided in combination with a nucleic acid sequence, or separately thereto. Where multiple enzyme doses are introduced, any one or more doses may be a combined enzyme/nucleic acid sequence dose. A preferred method comprises the introduction of i) a combined enzyme dose, and ii) a sequential dose of nucleic acid sequence. In a preferred embodiment, the enzyme dose comprises heparinase III and hyaluronan lyase.

Any suitable method may be used for introducing a nucleic acid sequence and enzyme to the sub-retina or vitreal cavity. A preferred method is injection. Thus, a dose of nucleic acid sequence and/or enzyme may be provided as an injection. A method of the invention may comprise injecting sub-retinally or into the vitreal cavity a nucleic acid vector comprising a nucleic acid sequence encoding a human photoreceptor protein. Preferably, the method is to provide a photoreceptor function to a cell, for example to restore vision, preferably for treatment of a retinal degenerative condition for example a retinal dystrophy including a rod dystrophy, a rod-cone dystrophy, a cone-rod dystrophy, a cone dystrophy and a macular dystrophy; another forms of retinal or macular degeneration, an ischaemic conditions, uveitis and any other disease resulting from loss of photoreceptor ability.

A method may comprise injecting into the vitreal cavity, separately, simultaneously or sequentially, i) a nucleic acid sequence encoding a photosensitive protein and ii) an extracellular matrix degradation enzyme. In a preferred embodiment, a method of the invention comprises injecting a single dose comprising a i) nucleic acid sequence encoding a photosensitive protein and ii) an extracellular matrix degradation enzyme into the vitreal cavity of an eye. Preferably, a method comprises injecting a single dose comprising i) a nucleic acid sequence encoding rhodopsin; and ii) the enzymes heparinase III and hyaluronan lyase, into the vitreal cavity of an eye. In a preferred embodiment, the invention provides a single injectable dose comprising i) a nucleic acid sequence encoding a photosensitive protein and ii) an extracellular matrix degradation enzyme for introduction into the vitreal cavity of an eye to provide a photoreceptor function to a cell, for example to restore vision, preferably for treatment of a retinal degenerative condition for example a retinal dystrophy including a rod dystrophy, a rod-cone dystrophy, a cone-rod dystrophy, a cone dystrophy and a macular dystrophy; another forms of retinal or macular degeneration, an ischaemic conditions, uveitis and any other disease resulting from loss of photoreceptor ability. Preferably, the invention provides a single injectable dose comprising i) a nucleic acid sequence encoding rhodopsin; and ii) the enzymes heparinase III and hyaluronan lyase, for introduction into the vitreal cavity of an eye to provide a photoreceptor function to a cell, for example to restore vision, preferably for treatment of a retinal degenerative condition for example a retinal dystrophy including a rod dystrophy, a rod-cone dystrophy, a cone-rod dystrophy, a cone dystrophy and a macular dystrophy; another forms of retinal or macular degeneration, an ischaemic condition, uveitis and any other disease resulting from loss of photoreceptor ability.

Where a nucleic acid sequence and one or more enzymes are provided in multiple (two or more) doses, these may be separated by suitable time intervals, for example 30 seconds to several hours or 1 or more days.

Each dose may comprise an effective amount of a nucleic acid sequence and/or an enzyme. An effective dose of a nucleic acid sequence may range from $1 \times 10^9$ to $1 \times 10^{14}$ or $7.5 \times 10^{15}$, preferably $1 \times 10^{11}$ to $7.5 \times 10^{13}$ nucleic acid sequences per treatment regimen (e.g. number of vectors or virus particles). An enzyme may be provided at a dose of 0.075-0.125 units per eye, or more.

A method of the invention may comprise a step of diagnosing a subject for a retinal degenerative condition, for example a retinal dystrophy including a rod dystrophy, a rod-cone dystrophy, a cone-rod dystrophy, a cone dystrophy, a macular dystrophy; another forms of retinal or macular degeneration, an ischaemic conditions, uveitis and any other disease resulting from loss of photoreceptor ability. A diagnostic step may comprise a visual test, for example a pupillary light reflex (PLR) test, visual acuity test (LogMAR), clinical diagnostic tests for example biomicroscopy/slit-lamp ocular/retinal clinical examination; colour vision testing, visual field testing, contrast/full field sensitivity; electrodiagnostic tests including for example EGGs, VEPs; imaging, retinal fundus photography, OCT, and adaptive optics scanning laser ophthalmoscope (AOSLO). Other suitable tests will be known to persons skilled in the art.

A method of the invention may comprise a step of dilating the pupil of an eye to be treated, for example by application of mydriatic, for example tropicamide and/or phenylephrine and/or cyclopentolate. A method of the invention may comprise a step of accessing the retina, for example by surgery.

A method of the invention may comprise monitoring the vision of a subject who has been treated for any improvement in vision. Improvements in vision may be any one or more of the following: increased pupillary light reflex (PLR), increased contrast sensitivity, increased resolution of low or high frequency flicker, and increased detection of moving images. In addition, increased light induced locomotor activity may be improved in animals such as mice. An improvement in vision may be an ability to respond to or detect light at $10^{15}$-$10^{13}$ photon/cm$^2$/s corneal irradiance. An improvement in vision may comprise an ON-sustained, ON-transient, OFF-excitatory, OFF-inhibitory or ON-OFF response. Preferably, monitoring improvement may comprise a method of quantifying the subjects subjective visual experience or an objective measure of light response, for example a pupillary light reflex (PLR) test, LogMAR visual acuity, clinical examination slit-lamp biomicroscopy; colour vision testing, visual field testing, contrast/full field sensitivity; electrodiagnostics-ERGs, VEPs; imaging: retinal fundus photography, OCT, adaptive optics scanning laser ophthalmoscope (AOSLO), or maze navigation tasks.

A subject may be monitored every 6, 8, 10, 12 or 24 hours, or every 2, 3, 4, 5 days. This may be repeated after 1, 2, 3, 4, 5, 6 months or a year or more.

The term "in vivo" refers to the natural environment (e.g., in an animal or a cell) and to processes or reaction that occur within that natural environment (for example on the body of a subject).

The present invention is based upon targeting a nucleic acid sequence encoding a photosensitive protein to retinal cells, to compensate for degeneration of photoreceptor cells in the retina. The cells to which the nucleic acid sequence is targeted are cells of the retina which are alive and capable of expressing a foreign nucleic acid sequence. Herein, a retinal cell is a cell of the retina, which is a nerve or neuron cell and is capable of becoming excited and transmitting an electrical signal. Preferably, a target retinal cell will be capable of generating an electrical signal and initiating the signalling cascade leading to transmission of signal to the optic nerve. Preferably, the target retinal cells are cells of the inner retina. A target cell may be a rod or cone cell, and/or may be a non-photoreceptor cell (i.e. a retinal cell which in its native form does not respond to light). A target retinal cell may include one or more cell types selected from the group consisting of rod cells, cone cells, ON-bipolar cells, OFF-bipolar cells, horizontal cells, ganglion cells, Muller cells and/or amacrine cells.

Thus, where a target retinal cell is targeted to an ON-bipolar cell, OFF-bipolar cell, horizontal cell, ganglion cell and/or amacrine cell of the retina, the expression of the nucleic acid encoding a photosensitive protein may be referred to as ectopic expression.

Thus, the present invention includes within its scope a method of ectopically expressing a nucleic acid sequence encoding a photosensitive protein in a non-photoreceptor cell. Such ectopic expression has the effect of providing photoreceptor function to a cell, by expression of a heterologous photosensitive protein therein. This serves to increase the photoreceptive capacity of the retina where degeneration is observed. The co-administration of extracellular matrix degradation enzymes with the nucleic acid sequence serves to improve transduction of the nucleic acid sequence into the target retinal cells.

A cell may be a prokaryotic or eukaryotic. It may be a bacterial cell such as E. coli, or may be a mammalian or non-mammalian cell, for example an insect cell, a yeast cell, a cell line or a cell free expression systems, for example for use in generating a vector or composition of the invention. A target retinal cell may be an ON-bipolar cell, an OFF-bipolar cell, a horizontal cell, a ganglion cell and/or an amacrine cell.

Horizontal cells are inner retina cells, involved in signal processing and feedback to photoreceptor cells; bipolar cells are inner retinal cells and communicate between rods/cone cells and the amacrine and/or ganglion cells; amacrine cells are found in inner retina and allow communication between photoreceptor pathway and ganglion cells; ganglion cells are innermost retinal cells which pass signal from photoreceptor cells to the optic nerve.

Reference to a cell herein includes progeny of the cell. Preferably, modifications to a cell according to the present invention also occur in succeeding generations of the transformed host cells. Progeny cells which may not be identical to the initial targeted cell but preferably will also exhibit expression of the non-native photosensitive protein.

The present invention may be used for the treatment of any disorder which is characterised by a degeneration of photoreceptor cells in the eye, typically a degeneration which is sufficient to result in partial or complete loss of vision. Examples of conditions which may be treated or ameliorated by the present invention include a retinal dystrophy (retinal pigmentosa) including a rod dystrophy, a rod-cone dystrophy, a cone-rod dystrophy, a cone dystrophy and a macular dystrophy; other forms of retinal or macular degeneration (e.g. age related macular degeneration), an ischaemic condition, edema (macular or retinal), uveitis and any other disease resulting from loss of photoreceptor ability.

As used herein, the term "subject" refers to any mammal or non-mammal. Mammals include but are not limited to, humans, vertebrates such as rodents, non-human primates, cows, horses, dogs, cats, pigs, sheep, goats, giraffes, yaks, deer, camels, llamas, antelope, hares, and rabbits.

Herein reference to "a" or "an" includes within its scope both the singular, and the plural, i.e. one or more.

Unless stated otherwise, the features and embodiments of each aspect applies to the other aspects of the invention, mutatis mutandis.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

EXAMPLES

In this study the feasibility of restoring light responsiveness to blind rd1 retinas by expressing human rod opsin in surviving inner retinal neurons using intravitreal AAV gene therapy was investigated. Both untargetted (neuron non-selective) and targeted (selective to ONBP cells) delivery was studied. Furthermore, the properties of restored responses in vivo and the ability of treated blind mice to resolve more sophisticated image processing including full field flickers, contrast detection, and naturalistic scenes were examined. Both untargetted and targeted ectopic rod opsin successfully recovers vision through a diverse visual code involving both ON and OFF pathways were found. Restored responses are transmitted beyond the retina into CNS visual pathways and function under the light intensity range of normal cone (and rod) vision as well as under light adapted conditions. The responses are robust enough to lead to light-induced locomotor behaviour in treated mice under illumination equivalent of indoor room lighting. Furthermore, the results show that mice with specifically targeted ON-bipolar cells, are able to resolve more complex visual functions including full field flickers, contrast detection and naturalistic movie scenes featuring changes in spatial patterns and object motion.

1. Intraocular Injections and Gene Delivery Via AAV (FIG. 1)

Adult C3H/HeJ (rd1) mice were used in this study. Specifically, a null mutation pde65b in rd1 mice leads to a complete loss of photoreceptors by p90 (Crater-Dawson et al, 1978, Farber db et al 1994). (Important to note that mutation does not affect rhodopsin itself). In order to answer whether rod opsin can express outside photoreceptors in vivo, the gene expression cassette was injected (FIG. 1A) intra-vitreally into adult rd1 mice. Bearing in mind translational potential of this approach a clinically safe AAV2/2 vector was used and a humanised version of rod opsin. Intravitreal injection was employed in order to achieve more widespread retinal transduction and minimise potential complications associated with an alternative sub-retinal delivery of vectors. Sub-retinal approach normally leads to transduction localised to the site of injection. An optimised combination of glycosidic enzymes was co-injected in order to enhance transduction and allow vector to penetrate deeper into the retina. It is unknown which cell types, if any, outside native photoreceptors would express rod opsin. Untargeted expression was studied first, using a strong pan-neuronal promoter, CAG.

Retinas were harvested four to six months post injection and retinal cryo-sections were immuno-labelled with antibody against human rod opsin. Expression was confirmed using fluorescent microscopy. Rod opsin expressed well outside photoreceptors as confirmed by strongly labelled cell somas (FIG. 1B). Expression was localised to the plasma membrane and was observed in both RGC layer (FIG. 1C) and INL (FIG. 1D). It is likely that with a non-selective promoter several different cell types in the INL were transduced, including some horizontal and amacrine cells, although by large the transduced cell bodies in the INL had characteristics of bipolar cells (FIG. 1D). Rod opsin expression was pan-retinal, albeit in the INL it was patchy with variable depths of penetration. In comparison, no fluorescence was seen in our control PBS injected group. In addition, the un-injected wild type retinas treated with antibody against rod opsin showed clear fluorescence in photoreceptor outer segments indicating that the antibody is specific for rod opsin with no off-target labelling.

Figure 2:
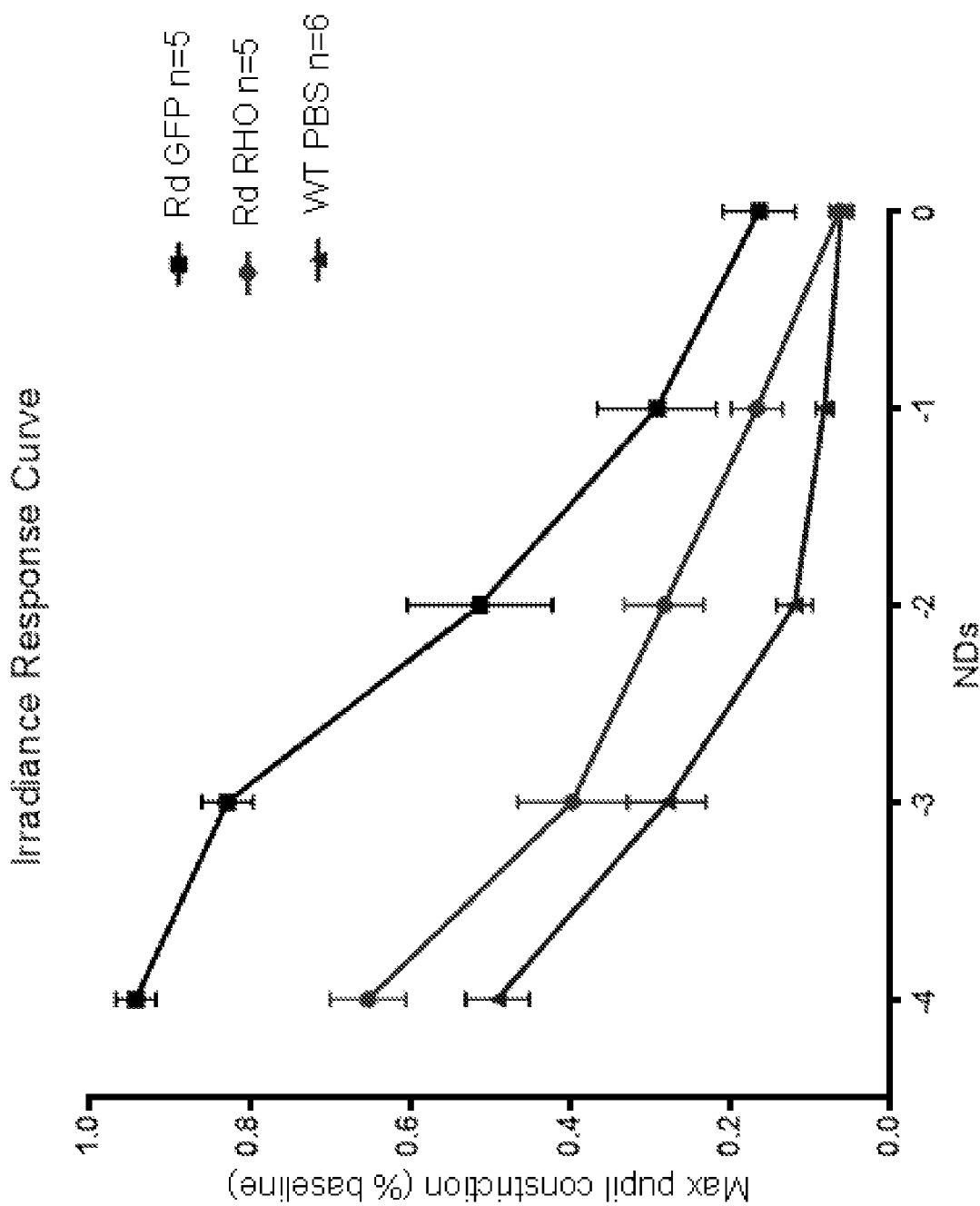
FIG. 2 shows restoration of pupillary light reflex following rhodopsin treatment.

Results:

Pupillometry:

FIG. 2. Restoration of pupillary light reflex following rhodopsin treatment. Irradiance-response curves for maximum pupillary constriction during 10 s of white light at neutral density filters ND4 (dimmest) to ND0 (brightest). Rhodopsin treated eyes (Rd RHO) show a marked improvement in visual sensitivity compared to GFP injected eyes (Rd GFP). Data for wild-type C57 mice injected with PBS/enzyme mixture are shown for comparison (WT PBS). Data are normalised to pupil size immediately preceding the onset of light. Values are mean±SEM, with n indicating the number of eyes examined.

In-Vivo Electrophysiology:

FIG. 3. Data from in-vivo electrophysiology recordings. Representative sample of peri-event histograms for a number of recording channels (sigs) showing the mean firing rate of LGN cells to 2 s stimulus of 405 nm light presented to a contralateral rhodopsin treated eye at increasing intensities (FIG. 3A—ND2, B—ND1, C—ND0; ND2=dimmest, ND0=brightest). A number of channels (e.g. sig 50, sig 52 at ND0 and ND1) showed robust 'fast-onset' light responses with an 'ON peak' after light is switched on, and an 'OFF peak' when light is switched off. The observed responses are clearly distinct from native light responses normally present in rd1 mouse LGN following stimulation of contralateral eye (FIG. 3). These native responses were observed from both rhodopsin or GFP treated eyes and show typical 'slow-onset' sustained, responses (from melanopsin retinal ganglion cells, FIG. 3D) and very transient fast responses (from surviving cone photoreceptors, FIG. 3E). The 'restored' responses (FIG. 3A-C) therefore come from retinal cells (retinal ganglion or bipolar cells) with induced photoreceptive properties from ectopic expression of rhodopsin.

Figure 5:
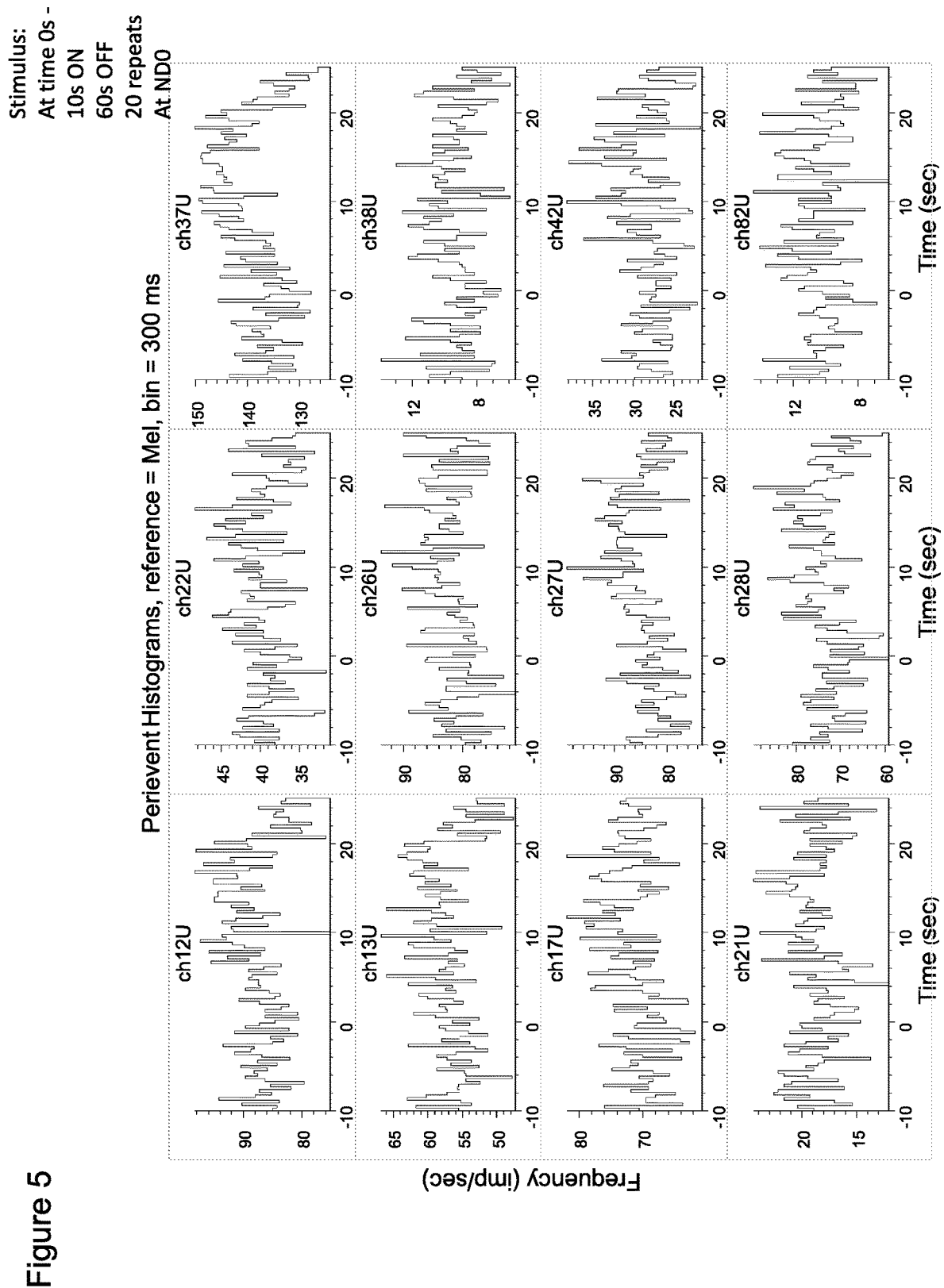
FIG. 5 shows the observed responses are clearly distinct from native light responses normally present in rd1 mouse retina following light stimulation.

MEA In-Vitro Recordings:

FIG. 4. Data from in-vitro MEA recordings. Representative sample of peri-event histograms for a number of recording channels (sigs) showing the mean firing rate of retinal ganglion cells to 2 s stimulus of 405 nm light applied to isolated retinas at increasing intensities (FIG. 4A—ND2, B—ND1, C—ND0; ND2=dimmest, ND0=brightest). A number of channels showed robust 'fast-onset' light responses with some channels (e.g. sig 35, sig 36 at ND0 and ND1) showing an 'ON peak' after light is switched on, and an 'OFF peak' when light is switched off. The observed responses are clearly distinct from native light responses normally present in rd1 mouse retina following light stimulation (FIG. 5). These native responses were observed from both rhodopsin or GFP treated eyes and show typical 'slow-onset' sustained responses (from melanopsin retinal ganglion cells, e.g. FIG. 5, sig 37). The novel responses (FIG. 4A-C) therefore originate from retinal cells with rendered photoreceptive properties from ectopic expression of rhodopsin.

Figure 13:
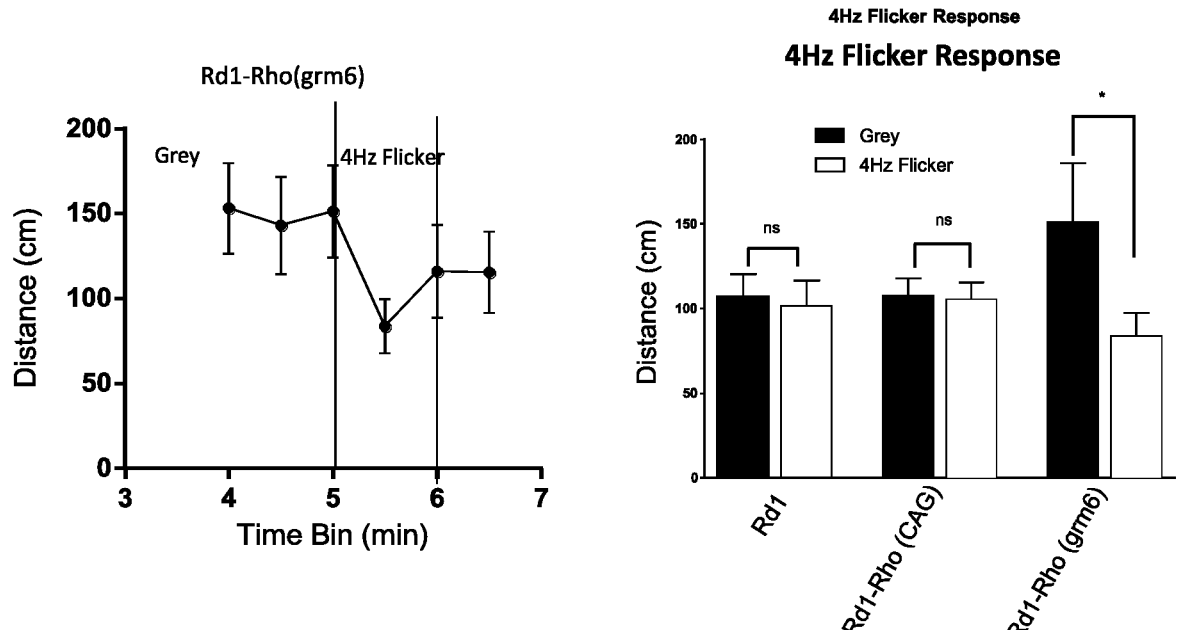
FIG. 13. A) Open box activity plots from grey screen light to 4 Hz flicker light for Rd1-grm6-hRho (n=5). Data are population mean of distance travelled in a preceding 30-second bin ±SEM. B) 4 Hz flicker response for Rd1-GFP (n=6), Rd1-CAG-hRho (n=6) and Rd1-grm6-hRho (n=5) mice. Paired histograms are shown for each group of mice depicting only the transition period from the entire activity plot (as shown for Rd1-grm6-hRho in F) from grey light (30 s just before the 4 Hz flicker) to 4 Hz flicker light (30 s just after the 4 Hz flicker). Data are population mean of distance travelled ±SEM. **p<0.005, paired Student t-test.

Restoring Light-Evoked Activity in Retinal Ganglion Cells—Functional Evaluation of Rod Opsin Responses In-Vitro Next, it was desired to confirm that the ectopically expressed rod opsin could drive functional light responses in the blind retina. Retinal explants were mounted onto multi-electrode array to test light evoked activity. Rod opsin injected (CAG-hRho) retinas from rd1 mice (4-6 m old) showed light responsive cells with robust initial firing rate after stimulation with two-second full-field flashes of broad spectrum white light at 15.4 log photons/cm2/s. However, after a few repeated presentations, light evoked activity diminished to low frequency of spiking, suggesting a bleaching effect. This was not surprising for in-vitro preparations where endogenous supplies of 9-cis are quickly depleted. However, addition of 9-cis to the preparation evoked robust neuronal activity with strongly reproducible responses. In addition, diverse response profiles were noted across the population of light responsive cells (n=6 retinas) including ON sustained, ON transient and OFF responses. In contrast, the GFP injected (CAG-GFP) age-matched control retinas showed no light evoked activity after presentation of the same light stimulus consistent with absence of photoreceptors (n=2 retinas). (It was also possible to drive light responses in rod opsin treated retinas at lower light intensities (14.4 log photons/cm2/s FIG. 1H and 13.4 log photons/cm2/s)) representing a significant improvement in light sensitivity compared to other optogenetic strategies which use at least 5-6 log units higher light intensities than necessary to activate native cone vision (Gaub, Lagali etc).

Ectopic Rod Opsin Mediated Responses are Transmitted to the LGN—Characterisation of Restored Responses In-Vivo (FIG. 3)

Figure 3F:
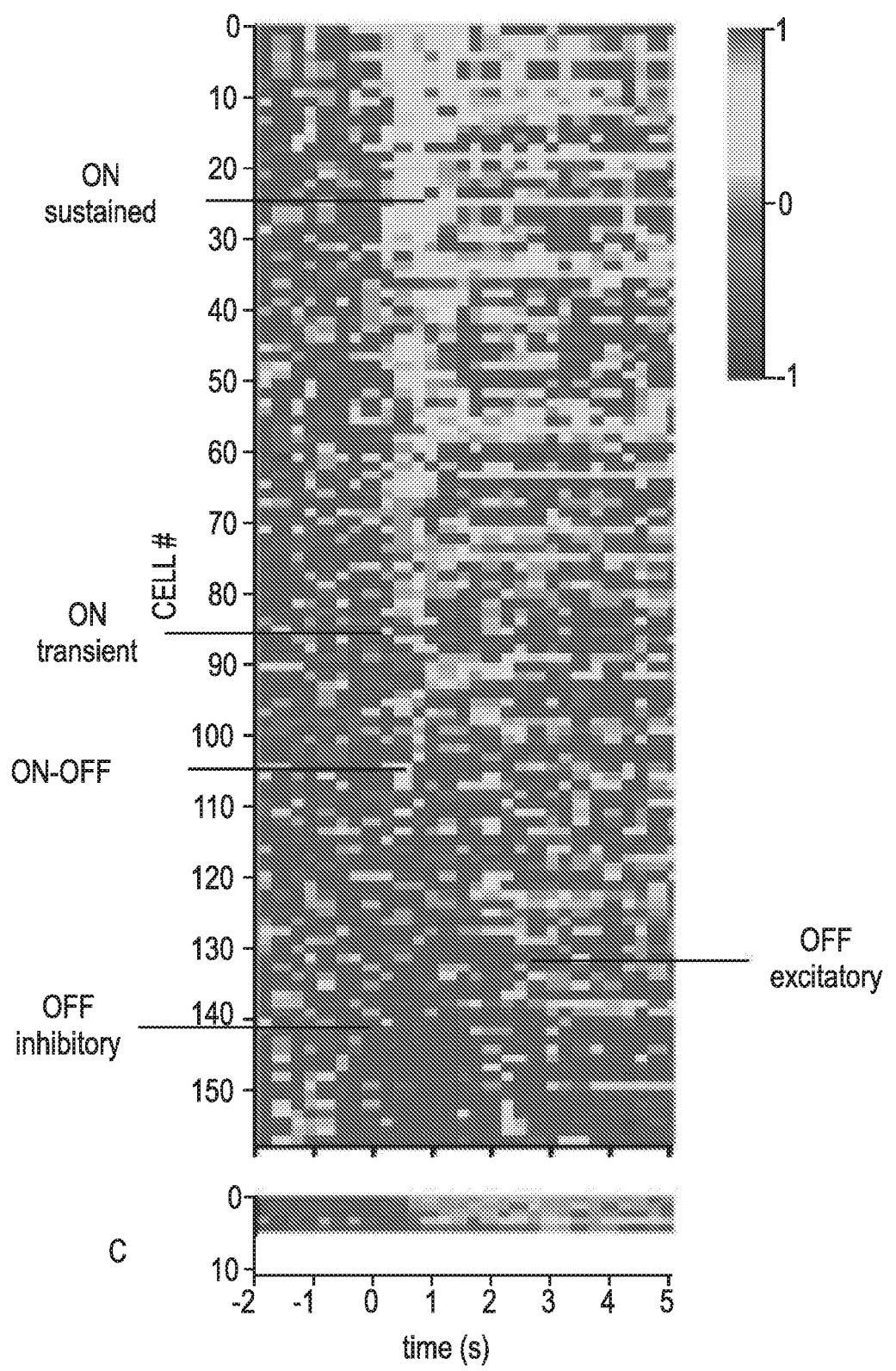
FIG. 3 A-E shows data from in-vivo electrophysiology recordings; F) Heat map of representative in-vivo dLGN light responses from Rd1 mice (n=5) where one eye was treated with rod opsin, CAG-hRho (B) and the other with GFP, CAG-GFP (C) depicting the diversity of restored responses: sustained, transient, ON and OFF. Responses were ordered according to the amplitude of sustained response during the initial 1 second of a 2 second light stimulus presentation (15.4 log photons/cm2/s); G-J) Representative peri-stimulus time histograms (PSTHs) showing average response to multiple presentations of full field flashes (15.4 log photons/cm2/s) for ON-sustained (G), ON-transient (H), OFF (I) and ON-OFF (J). Corresponding trial bin counts (TBCs) are shown on top of each PSTH.

Since rod opsin bleaching, without constant exogenous supplies of chromophore (9-cis retinal), was a problem for in-vitro experiments neuronal activity was tested in-vivo in order to determine if there would be enough retinal in intact retinas to allow the chromophore recycling and prevent bleaching. In addition, whether or not the restored responses are robust enough to activate higher visual centres in the context of degenerating and remodelling retina was investigated. Neuronal responses from the dorsal lateral geniculate nucleus, dLGN, were recorded from both hemi-spheres simultaneously, where one eye was previously treated with rod opsin and the other, injected with GFP, served as an internal control. The dLGN is the major retinorecipient part of the brain and contains the neurons that relay signals to the visual cortex. Responses from the dLGN, the first synaptic connection for the RGCs, were studied to get the best idea of the properties of restored responses. A significantly increased number of light responses across the dLGN (157) were found compared to internal controls (4) following two-second full-field flashes of 410 nm light at 15.4 log photons/cm2/s. Light responsive cells were identified according to objective criteria using peri-stimulus time histogram (PSTH) analysis in the Neuroexplorer (Nex Technologies) where average firing rate had to cross 95% CI after stimulus onset or offset, compared to the baseline. PSTH time interval for 2 s stimulus was −2 s to 5 s, and bin size 250 ms. Clear artefacts leading to false positives were excluded. 'Heat-maps' were generated to include all light responsive cells from each group and order responses according to the amplitude of the sustained response during the initial 1 second of a 2-second stimulus presentation. Green colours (+1) represent high firing rates and pink/purple colours (−1) low firing rates. FIG. 3F clearly depicts a diverse nature of restored responses including sustained, transient, ON and OFF responses, as are normally found in WT retinas. In contrast, light responsive cells (n=4) that were found in the control group were all slow onset ON sustained, likely to originate from native ipRGCs. Bleaching was not found to be a problem for in-vivo light responses, which showed robust firing across many repeated trials.

To capture the diversity of restored responses seen at a single unit level (but found across all retinas tested) individual responses were studied systematically through their peri-stimulus time histograms (PSTH) and corresponding trial bin counts (TBC). Averaging across the population of cells would be difficult given that some cells are excited by light ON (ON responses) some inhibited by light ON (OFF inhibitory responses), some excited by light OFF (OFF excitatory) and some excited by both light ON and OFF (ON-OFF cells). Both sustained (10 s and 2 s light step, FIG. 3G) and more transient responses (2 s light step, FIG. 3H) were evoked in treated eyes, comparable to those from WT retinas (insert). In addition, to ON responses we also found many OFF responses (FIG. 3I) and some ON-OFF responses (FIG. 3J). Across the population of light responsive cells, 99/157 (63.1%) of ON cells, 46/157 (29.3%) of OFF cells and 12/157 (7.6%) of ON-OFF cells (FIG. 3E) were found. These were broadly categorised into ON sustained cells (51/157; 32.5%), ON transient cells (48/157; 30.6%), OFF excitatory cells (29/157; 18.5%), OFF inhibitory cells (17/157; 10.8%) and ON-OFF cells (12/157; 7.6%). Mean firing rate ranged between 20-100 Hz across the restored responses. Responses were found with short latencies (onset within 50-100 ms—2D, cell 1; 2E cell1) as well as longer latencies (onset within 500 ms—2D, cell 3). Firing rate for most sustained responses returned rapidly back to baseline (hundreds of millisecond of turning the light stimulus off, 2D cell 3) although it was found some cells with more persistent firing (seconds after light off, 2D cell 2). (similar to other studies, lagali, flannery, wt responses)

Sensitivity and Contrast Features of Restored LGN Responses

Figure 6:
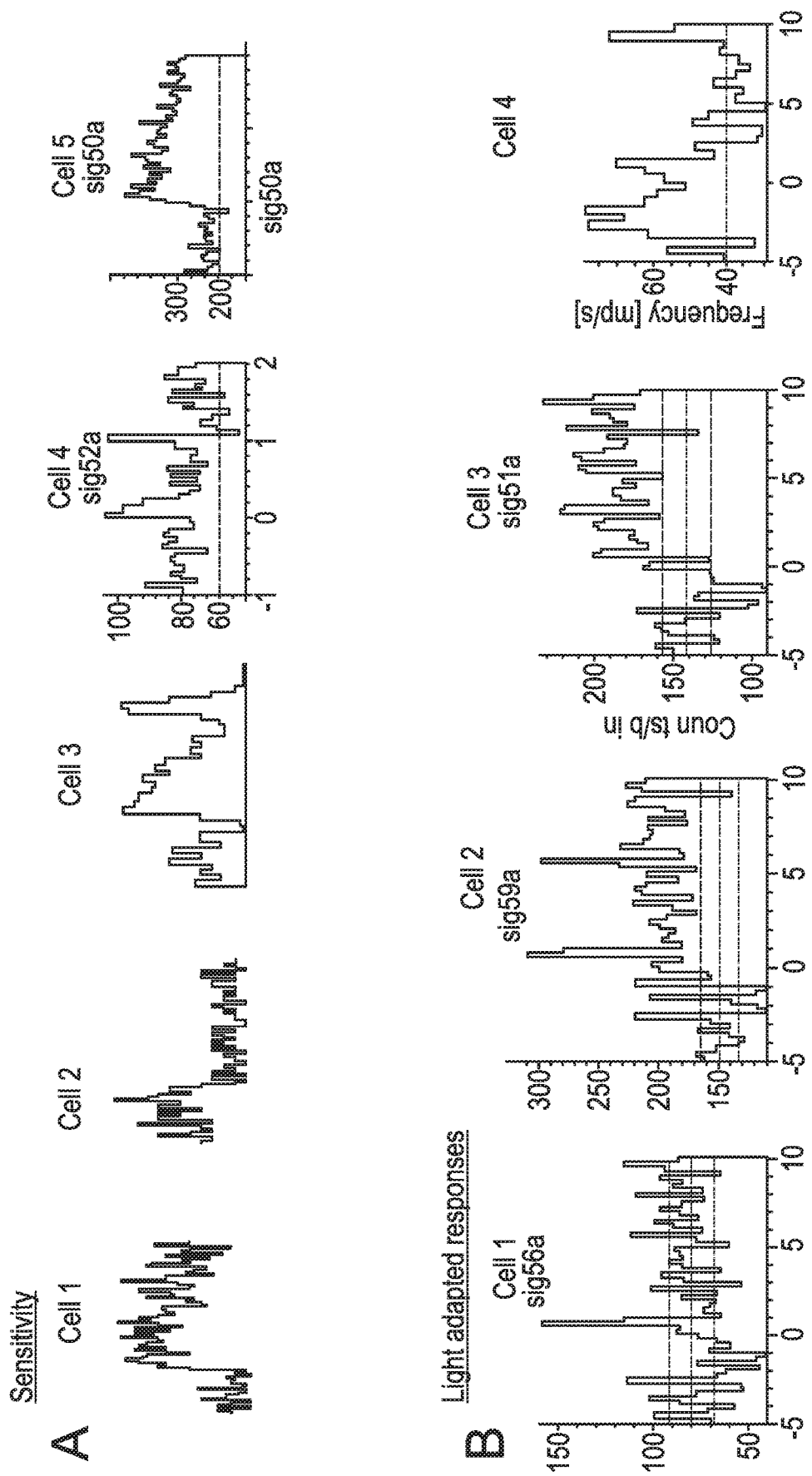
FIG. 6 shows dLGN responses in rd1 mouse driven by rod opsin treated eyes respond over a range of light intensities and in light adapted conditions A) Sensitivity response profile (PSTH and TBC) of five representative dLGN units from Rd1-CAG-hRho mice presented with full field flashes at different light intensities (ND2=13.4, ND1=14.4 and ND0=15.4 log photons/cm2/s); B) Contrast sensitivity response profile (PSTH and TBC) of four representative dLGN units from Rd1-CAG-hRho mice recorded under light adapted conditions (Michelson contrast 96% @ ND0=15.4 log photons/cm2/s).

Current optogenetic strategies based on ChR ($10^{15}$-$10^{17}$ photons/cm$^2$/s) and photosynthetic switches ($10^{15}$-$10^{18}$ photons/cm$^2$/s) require high light intensities for activation and long-term exposure of these light intensities may be detrimental to the retina. In our experiments, restored neurons operate under a dynamic range of light intensities equivalent to natural daylight illumination ($10^{13}$-$10^{15}$ photons/cm$^2$/s) (FIG. 6). Importantly robust, repeatable sustained and transient, ON and OFF responses were found across these light intensities, indicating how sensitive the system is. Some light responses were also found at lower light intensities ($10^{12}$ and $10^{11}$, although these were not as readily/as well/poorly reproducible (data not shown). No convincing light responses were recorded at levels lower than $10^{15}$ photons/cm$^2$/s when untreated rd1 retinas were stimulated.

So far, studies on novel optogenetic tools have all characterised restored responses under dark-adapted conditions, using full field light steps from darkness. Although this increases the possibility of evoking strong neuronal responses, these conditions are rarely present in real life scenarios. The system was tested under more natural conditions, in light adapted states. Robust, high amplitude, repeatable responses were recorded under light adapted conditions, Michelson contrast 96% (FIG. 6B). No contrast detecting cells were found in response to light adapted stimulation of control rd1 retinas.

(Lower contrasts (66% and 33%,) also evoked measurable responses, although these were not as highly reproducible across repeated trials (see supplemental/or not show).

Restricting Ectopic Expression of Rod Opsin Using a Cell Specific Promoter

Figure 7:
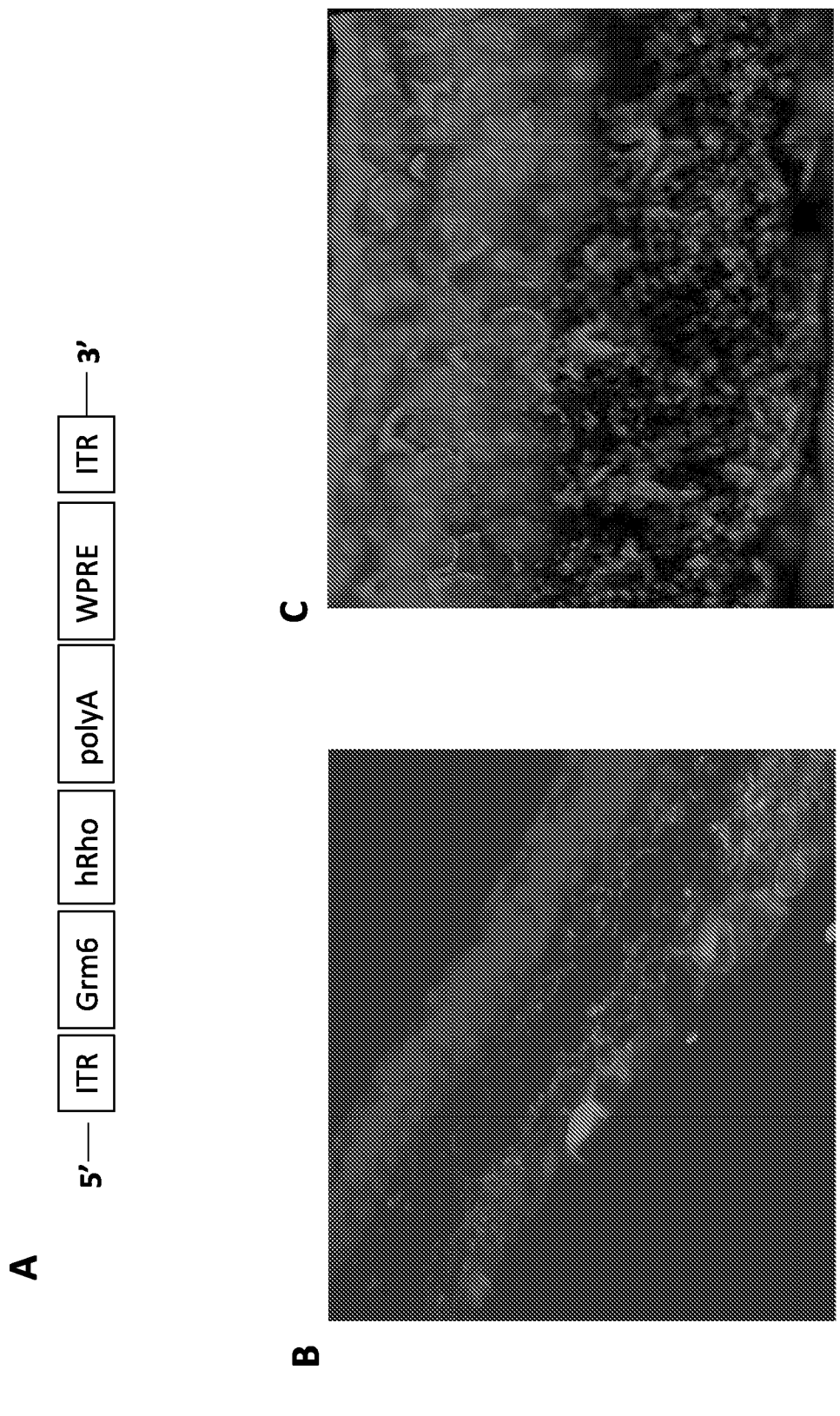
FIG. 7 shows targeted expression of rod opsin to ON bipolar cells restores visual responses in blind rd1 retinas: A) AAV2 vector DNA construct driving targeted expression of human rod opsin under Grm6 promoter; B, C) Exemplar fluorescent microscope images of a section through the mouse retina after intravitreal delivery of viral vector in A in conjunction with glycosidic enzymes that break down the extracellular matrix (B). High magnification fluorescent images depicting membranous localization of rod opsin in cell somas of INL cells (C). Retinas were treated with α-hRho antibody (red) and nuclei were stained with DAPI (blue). Calibration bar=50 μm. GCL=ganglion cell layer, IPL=inner plexiform layer, INL=inner nuclear layer.

The diversity of the generated visual code with unrestricted ectopic expression of rod opsin was encouraging. However, it was decided to investigate if there would be any changes to this code if rod opsin expression was restricted to "ON pathway" only. Therefore, rod opsin was expressed in ON bipolar cells using a cell specific Grm6 promoter (FIG. 7A-C).

Figure 8:
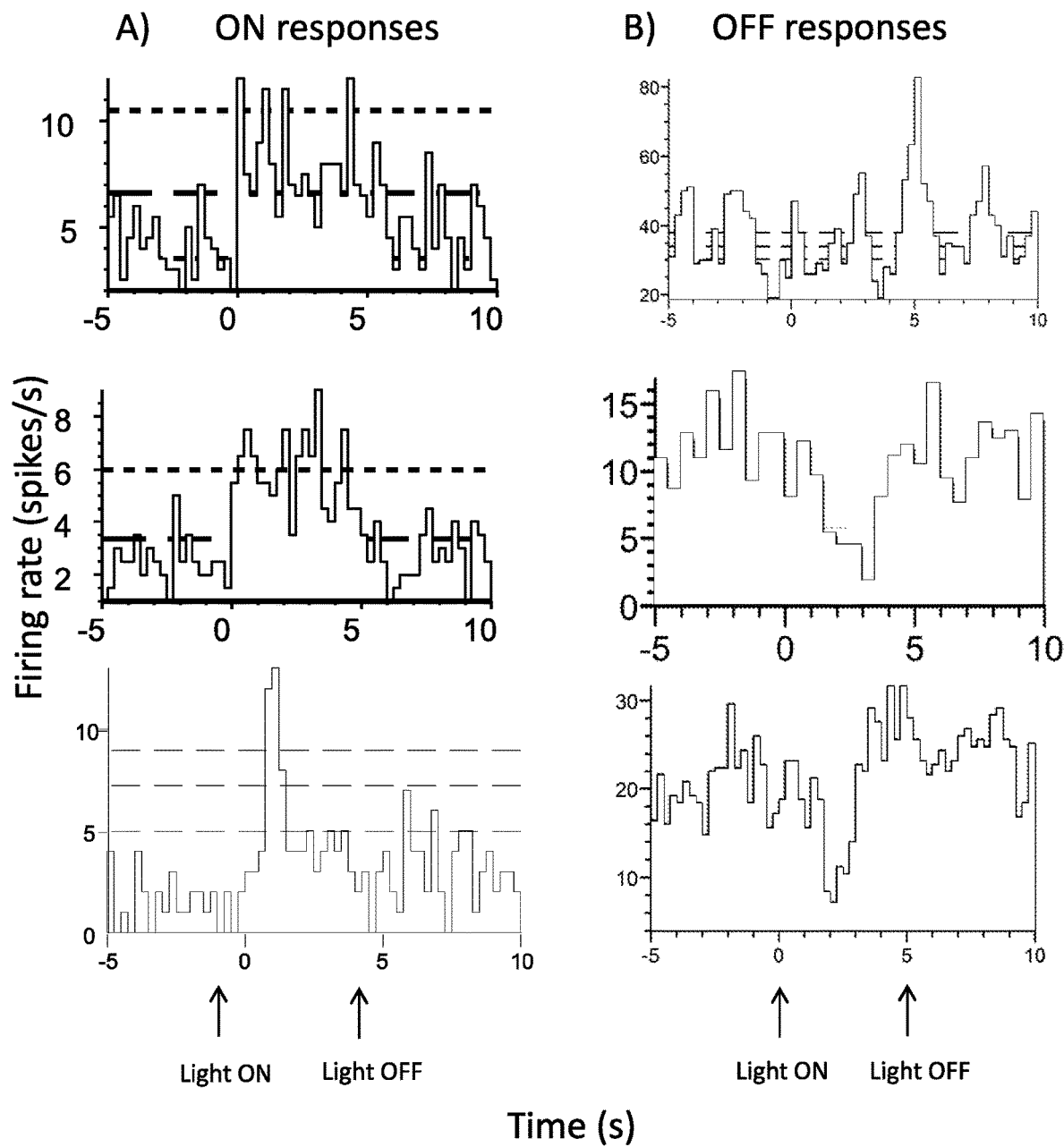
FIG. 8 shows representative peri-stimulus time histograms (PSTHs) showing average responses to multiple presentations of 5-second full field flashes @ND0=15.4 log photons/cm2/s for ON (A) and OFF (B) responses.
Figure 9:
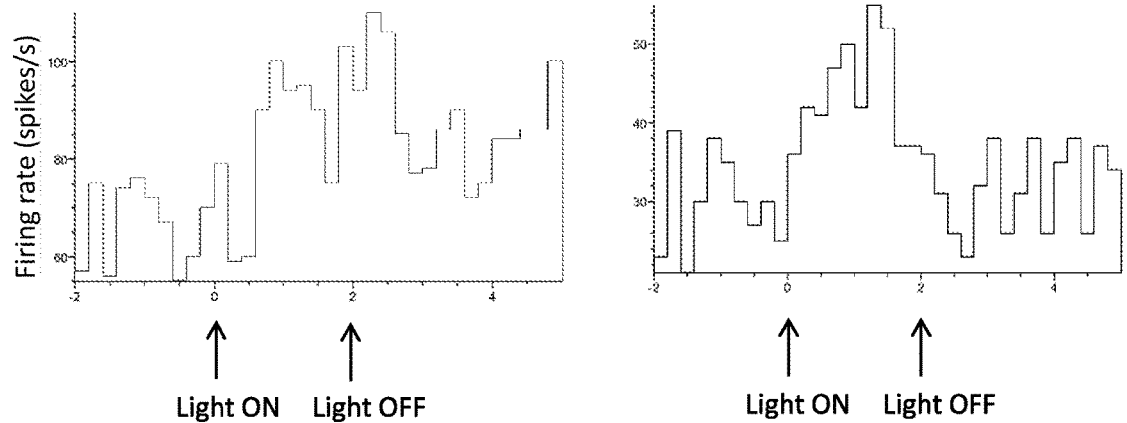
FIG. 9 shows representative peri-stimulus time histograms (PSTHs) showing average responses to multiple presentations of 2-second full field flashes @ lower light levels (ND2-13.4 log photons/cm2/s).
Figure 10:
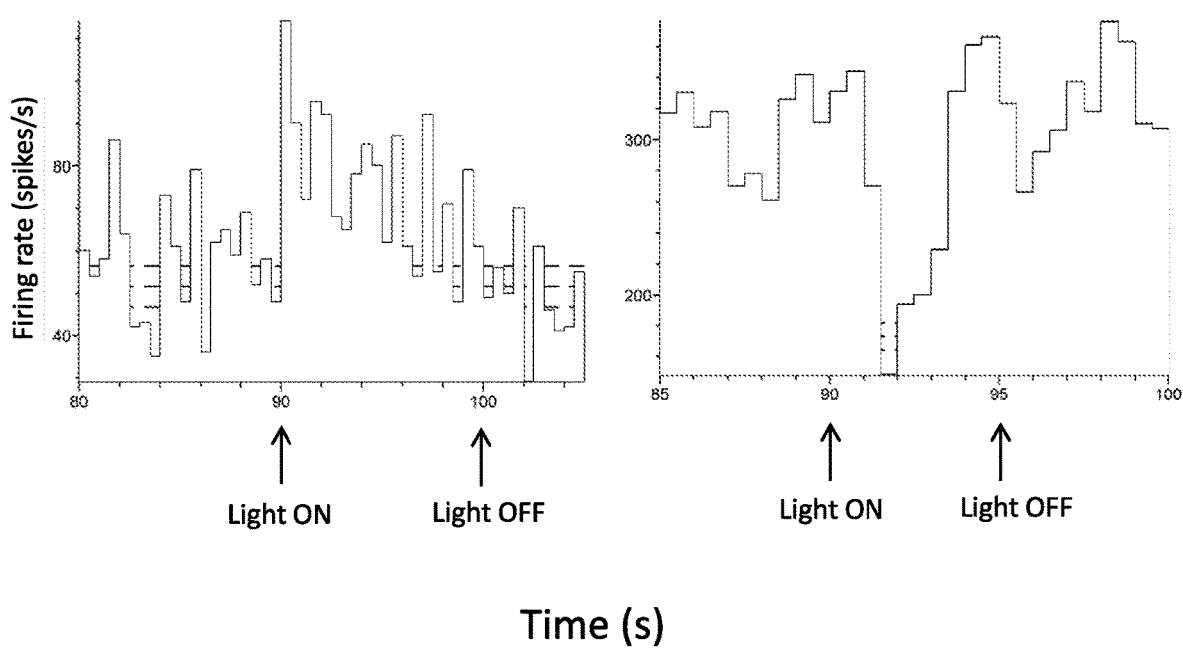
FIG. 10 shows representative peri-stimulus time histograms (PSTHs) showing average responses to multiple presentations of 5-second full field flashes under light adapted conditions—Michelson contrast 96%.

FIGS. 8-10 show restored dLGN light responses under various light conditions for mice that have been treated with rod opsin targeted to ONBP cells. Sensitivity was demonstrated down to normal lighting conditions. Figures for irradiance quoted are for corneal measurements. Retinal irradiance will be approximately one order of magnitude lower.

In-vivo LGN recordings from these mice also show a significantly increased number of light responses (n=100) compared to internal controls (n=6) following stimulation with full field flashes (2 s) of 410 nm light at 15.4 log photons/cm2/s. Once again, a range of response profiles was observed—sustained, transient, ON and OFF (excitatory and inhibitory) in the rod opsin treated group. Compared to untargeted responses, light responses from targeted ON-BP cells were more evenly distributed between ON and OFF types. Across the population of light responsive cells we observed 48/84 (57.1%) of ON responses and 36/84 (42.9%) of OFF responses. These were broadly subdivided into ON sustained cells (34/84; 40.5%), ON transient cells (14/84; 16.6%), OFF excitatory cells (6/84; 7.1%) and OFF inhibitory cells (30/84; 35.7%). More detailed characterisation of restored light responses showed fast ON-transient, ON-sustained and OFF-transient responses (onset within hundreds of ms) and slower OFF-inhibitory responses (onset within seconds).

These delayed robust OFF inhibitory responses were a specific feature of targeted rod opsin expression (4G cell 2 and 3).

It was next investigated if the sensitivity and contrast detection of ON-bipolar driven responses is similar to our untargeted group. Comparable sensitivity profile of ON-bipolar driven responses was found to the non-selective/untargeted group and light responses at 13.4 log photons/cm2/s (FIG. 4H) were recorded. Similarly, in light adapted conditions, we also found cells responsive to Michelson contrast level (96%, FIG. 4I).

(Lower amplitude and less reproducible responses were recorded at lower contrast levels (66% and 33%), similar to those observed from untargeted retinas (data not shown))

Light-Induced Behavioural Responses

Next, it was investigated whether the visual information transmitted to the brain, driven by both untargeted and targeted ectopic rod opsin transduction, could restore lost visual functions in blind rd1 mice. First, a simple behaviour response to light, the pupillary light reflex (PLR) was tested. This reflex is normally mediated by melanopsin expressing ipRGCs (Lucas R J, et al Science. 2003 Jan. 10; 299(5604): 245-7.) and is retained at high threshold in rd1 mice after photoreceptor degeneration (Lucas R J, et al Nat Neurosci. 2001 June; 4(6):621-6., Lin B, Proc Natl Acad Sci USA. 2008 Oct. 14; 105(41):16009-14.). Irradiance-response curves were recorded for maximum pupillary constriction during ten seconds of white light at a range of light intensities (FIG. 11A). Impaired PLR was found in GFP injected, control mice, confirming previous findings. Unrestricted rod opsin expression restored PLR comparable to wild type behaviour (FIG. 11A-D). However, with the targeted expression, the PLR remained largely impaired (FIG. 11A-C).

Figure 12:
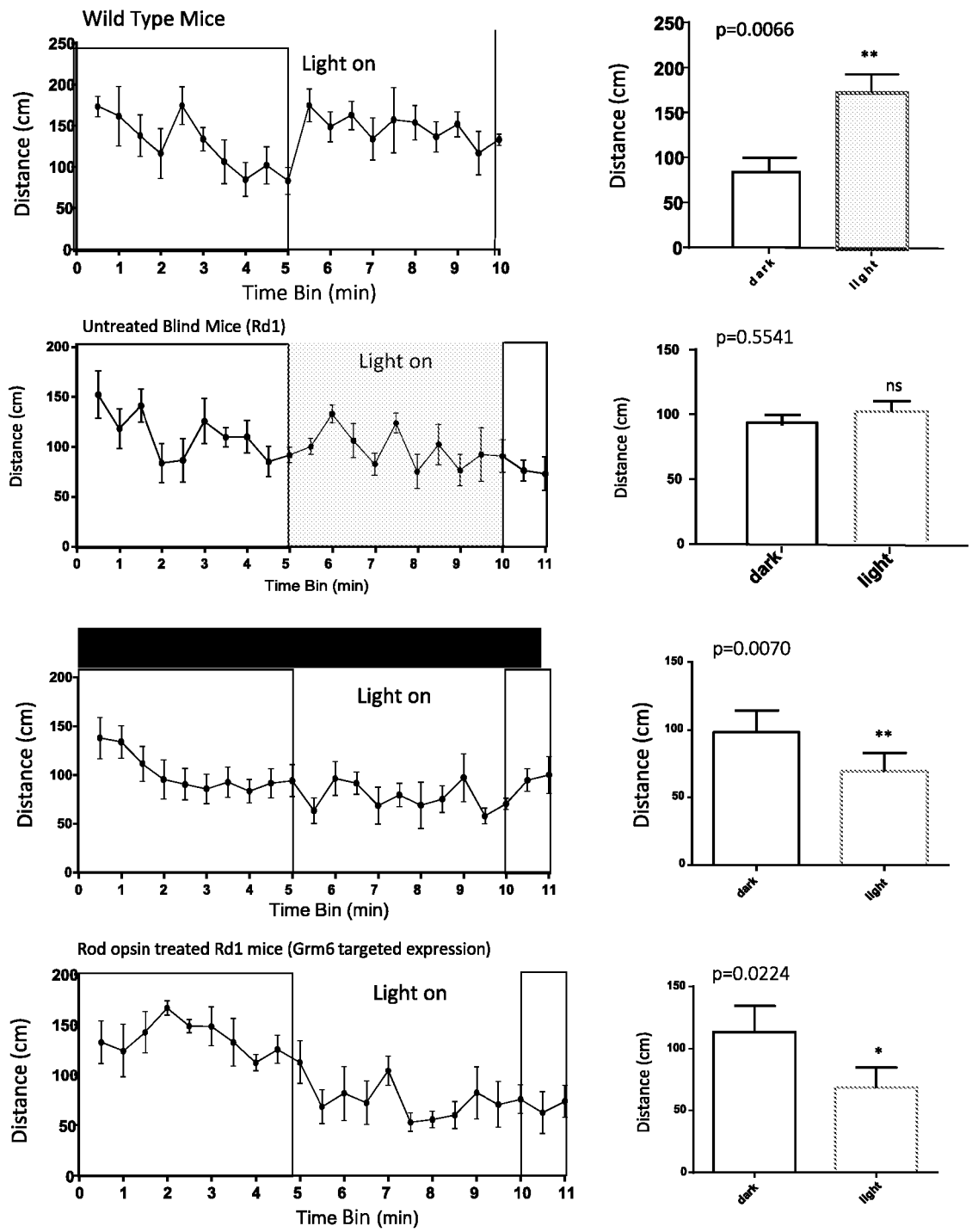
FIG. 12 shows open box activity plots from dark (shaded in dark) to light (white area) for the four groups of mice: WT n=5; Rd1-GFP n=6; Rd1-CAG-hRho n=6; Rd1-grm6-hRho n=5. Values in the plots are population means of distance travelled in a preceding 30-second bin ±SEM. Histograms on the right show mean distance travelled across the population for the transition period from dark (30 s just before the light; dark bars) to light (30 s just after the light; white bars). Error bars are SEM. *p<0.05, **p<0.005, paired Student t-test.

It was then asked whether the restored optogenetic visual code could support more complex visual discrimination at behavioural level. Motivated by classical open-field light/dark box tests (Bourin M, Hascoët M (2003), Eur J Pharmacol 463(1-3): 55-65. the locomotor behaviour in response to various artificial and natural light stimuli was measured. Mice were placed in an open field modified light/dark box and allowed free movement between two arenas via an opening in the separating wall. Flat screen computer monitors outside each arena were used to display a variety of visual stimuli. The light intensities of our stimuli were equivalent of indoor lighting levels (range from 0.00132 W/m2 for black screen to 0.116 W/m2 for white screen). Simple dark-light discrimination was first tested. After initial habituation to the novel environment (3 min) mice were allowed to explore the box for 5 minutes in dark (dark screen radiance=0.004072 $Wsr^{-1}m^{-2}$; irradiance=0.00132 W/m2), followed by 5 minutes in white light (white screen radiance=0.06526 $Wsr^{-1}m^{-2}$; irradiance=0.116 W/m2). The locomotory assay was first evaluated in wild-type mice where activity plot shows a significant increase in locomotion in the first 30 s of transition from dark to light (FIG. 12, mean distance in dark=24.46±7.00 cm; mean distance in light=147.5±5.09 cm; p=0.0066). Blind rd1 mice showed no significant change in activity during this dark-light transition (mean distance in dark=91.75±7.70 cm; mean distance in light=100.2±8.145 cm p=0.5541). However, activity plots for the treated groups, rd1-hRho-CAG and rd1-hRho-grm6, display a sudden decrease in motor activity when light is turned on. This light-induced 'freezing' behaviour was significant in the first 30 s of transition from dark to light (for rd1-hRho-CAG, mean distance in dark=98.40±16.12 cm; mean distance in light=69.73±13.32 cm; p=0.0070; for rd1-hRho-grm6 mean distance in dark=112.9±21.47 cm; mean distance in light=68.37±16.81 cm; p=0.0224).

After establishing that the treated mice can distinguish light from dark, their behaviour in response to more dynamic visual stimuli was tested. Locomotor activity in light adapted conditions (5 minutes of exposure to gray screen light, radiance=0.03342 $Wsr^{-1}m^{-2}$; irradiance=0.0663 W/m2) was compared to full field flicker at 4 Hz (FIG. 13A). Rd1-hRho-grm6 group was able to resolve this flicker frequency (mean distance in gray=151.3±34.95 cm; mean distance in flicker=83.7±13.76 cm; p=0.0466), whereas rd1-hRho-CAG and untreated blind mice showed no change in behaviour (FIG. 13B). We then tested rd1-hRho-CAG at a lower frequency, at 2 Hz and found that they do respond (likely limit of this system) (data not shown).

Figure 14:
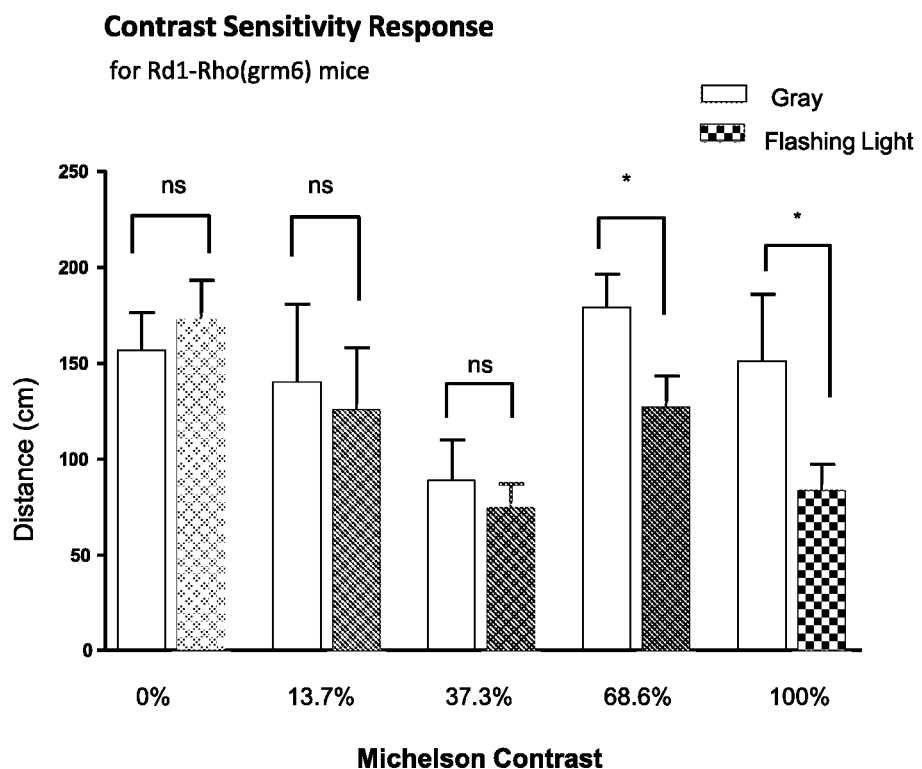
FIG. 14 shows Contrast sensitivity response for the Rd1-grm6-hRho mice (n=5) showing distance travelled before and after 4 Hz flicker at different Michelson contrasts. For each contrast performance, only the transition period from the activity plot is shown depicting the distance travelled in the 30 s before (white bars) and in the 30 s after the presentation of flicker (chequered bars). Data are population mean of distance travelled ±SEM. *p<0.05, **p<0.005, paired Student t-test.

As the targeted rd1-hRho-grm6 mice had the best response with full field flicker this group was further tested to see if mice can discriminate more subtle changes in light and detect contrast. Indeed it was showed that mice responded at different Michelson contrasts (FIG. 14; mean distance in gray=179.3±17.34 cm; mean distance in flicker=127.2±16.29 cm; p=0.0238 At 68.6% contrast and mean distance in gray=151.3±34.95 cm; mean distance in flicker=83.7±13.76 cm; p=0.0466 at 100% contrast).

Figure 15:
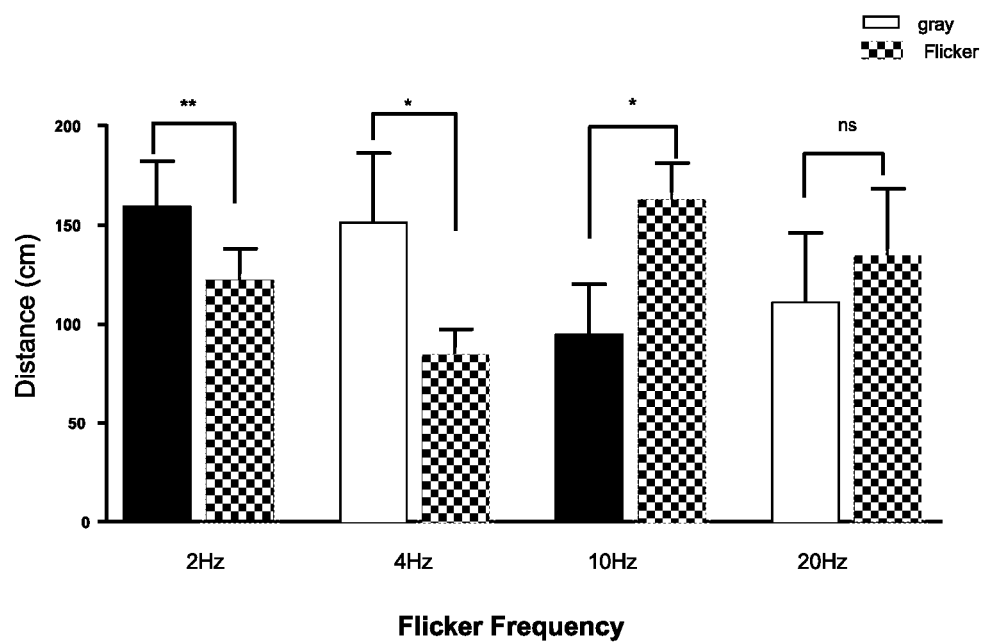
FIG. 15 shows flicker frequency response for the Rd1-grm6-hRho mice (n=5) showing distance travelled before and after presentation of full field flicker light at different frequencies. For each flicker response, only the transition period from the activity plot is shown comparing the distance in the 30 s before (grey bars) to the distance in the 30 s after the presentation of flicker (patterned bars). Data are population mean of distance travelled ±SEM. *p<0.05, **p<0.005, paired Student t-test.
Figure 17:
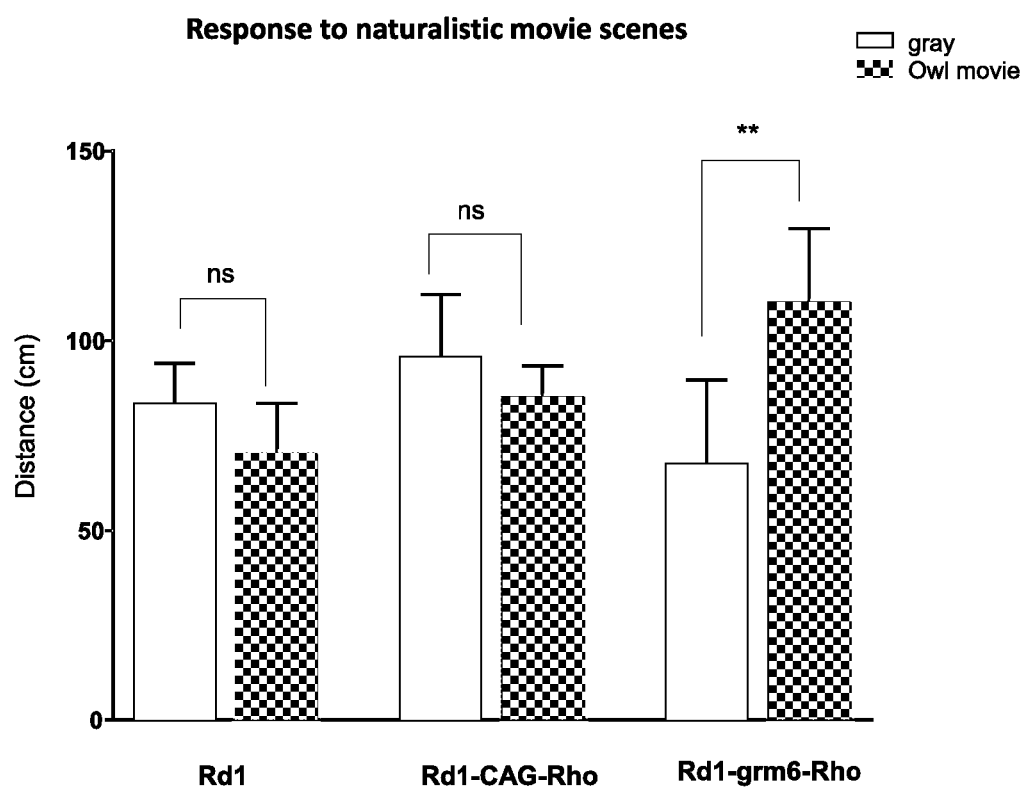
FIG. 17 shows naturalistic movie response for Rd1-GFP (n=6), Rd1-CAG-hRho (n=6) and Rd1-grm6-hRho (n=5) mice. Paired histograms are shown for each group of mice depicting only the transition period from the entire activity plot from grey light (30 s just before the movie presentation; white bars) to owl movie (30 s just after the movie; black bars). Data are population mean of distance travelled ±SEM. **p<0.005, paired Student t-test.

Higher flicker frequencies in rd1-hRho-grm6 mice were also looked at, 10 Hz and 20 Hz. No response at 20 Hz was found but convincing response at 10 hz (FIG. 15; mean distance in gray=93.64±26.39 cm; mean distance in flicker=162.6±18.57 cm; p=0.039 at 10 Hz).

Responses to Naturalistic Scenes

Having described characteristics of restored responses using a variety of artificial stimuli, it was set out to determine whether ectopic rod opsin could drive visual responses at brain level under more naturalistic scenes with spatial properties. To this end, a naturalistic movie was projected (mice moving around an open arena) to Rd1-CAG-hRho and Rd1-grm6-hRho anaesthetised mice and recorded in-vivo responses from the LGN. The 30-second movie was presented repeatedly over a 30-minute period allowing identification of cells with reproducible firing patterns over many presentations. Individual neurons whose firing rate is modulated by particular features of the movie scene after stimulation of both untargeted and targeted retinas (FIG. 16A to C) were observed; no 'movie-responsive' neurons from the control eyes.

It was then investigated whether mice can see the naturalistic scenes? In an open field behavioural locomotory assay, a naturalistic movie featuring a looming owl was presented to the mice in the test box. Indeed it was found that the rd1-hRho-grm6 mice responded to a looming owl (FIG. 6C) showing a significant change in locomotor behaviour in a 30 s transition from uniform light to a movie scene (FIG. 14; mean distance in gray=67.68±22.05; mean distance in natural movie=110.2±19.44; p=0.0079). Interestingly they did not display freezing behaviour, but indeed increased their motor activity, likely in an attempt to escape from the predator. No changes were found in behaviour in response to a movie in blind Rd1 mice or Rd1-hRho-CAG mice.

Materials and Methods

Animals

These mice are a model of severe and rapid form of retinal degeneration, similar to some forms of retinitis pigmentosa in humans (McLaughlin et al., 1993). All animal experiments were conducted in accordance with the UK Home Office regulations for the care and use of laboratory animals, the UK Animals (Scientific Procedures) Act and the Animal Welfare Body of the University of Manchester. Animals were kept under a 12 hour light:dark cycle and supplied with food and water ad libitum.

Gene Delivery Via AAV

Intraocular injections were carried out in mice at six weeks of age under general anaesthesia using isofluorane. Prior to injections, pupils were dilated with tropicamide and phenylephrine. A custom made ultra-fine needle (Hamilton RN needle 34 gauge, supplied by ESSLAB) was attached to a 5p1 Hamilton glass syringe and was passed at 45 degrees through the pars plana into the vitreous cavity, carefully avoiding the lens and blood vessels. The injection was performed under a direct visualisation of the needle tip through cover-slipped eyes under the operating microscope. The vectors, rAAV serotype 2 (rAAV2/2, or simply AAV2) expressing rod opsin or GFP under the control of a strong ubiquitous pan-neuronal promoter (CAG) or ON-bipolar cell specific (Grm6) promoter were obtained from Vector Biolabs, Philadelphia, USA. The CAG promoter is a fusion of CMV early enhancer and chicken β-actin promoter. The Grm6 promoter is a fusion of 200-base pair enhancer sequence of the mouse Grm6 gene encoding for ON-bipolar cell specific metabotropic glutamate receptor, mGluR6, and an SV40 eukaryotic promoter. The gene of interest in each case was flanked by inverted terminal repeat (ITR) domains and stabilised by polyadenylation signal sequence (polyA) and a woodchuck hepatitis posttranscriptional regulatory element (WPRE).

One eye of each mouse was injected with rod opsin expression construct (either AAV2-ITR-CAG-hRho-polyA-WPRE-ITR for untargeted expression or AAV2-ITR-grm6-hRho-polyA-WPRE-ITR for targeted expression) and the other with GFP expression construct (either AAV2-ITR-CAG-GFP-polyA-WPRE-ITR for untargeted expression or AAV2-ITR-grm6-GFP-polyA-WPRE-ITR for targeted expression). Each eye received 3 µl of viral construct containing $1\times10^{13}$ genomic counts, in combination with 0.5 µl of glycosidic enzyme solution containing 0.125 units of heparinise III (E.C. 4.2.2.8) and hyaluronan lyase (E.C. 4.2.2.1) obtained from Sigma-Aldrich, Dorset, UK. The enzyme solutions were made fresh on the day of injection by dissolving the enzymes in sterile phosphate-buffered saline (PBS). The vector and enzymes were mixed in a syringe immediately before an eye injection and were given in a single combined injection.

Tissue Processing, Immunohistochemistry and Bioimaging

For tissue processing, retrieved eyecups (>6 weeks post vector injection) were fixed in 4% paraformaldehyde (PFA) for 24 hours at 4° C. The tissue was then washed in PBS and further fixed in 30% sucrose in PBS overnight at 4° C. Fixed eyes were cryo-protected in optimal-cutting temperature medium (Raymond A Lamb Ltd., Eastbourne, UK) and frozen at −80° C. until further processing. Cryo-protected retinal section were cut on a cryostat (Leica, Microsystems) horizontally through the eyecup @8-10 µm thickness from ventral to dorsal side, so that each section contained a complete nasal to temporal cross-section of the retina. Ten-twelve sections were collected on each slide containing sections representative of the entire retina. Slides were stored at −80° C.

For immunohistochemistry, slides were removed from freezer and allowed to air-dry at room temperature for 1 hour. Sections were permeabilised by immersing slides in PBS with 0.2% Triton for 20 minutes at room temperature. Following this sections were background blocked with PBS with 0.2% Triton X-100 containing 10% donkey serum (D9663; Sigma, UK) for 1 hour at room temperature. Primary antibody (Rabbit Anti-Human Rhodopsin, Abcam, Ab112576) was applied at 1:200 dilution in blocking buffer (PBS with 0.2% Triton X-100 and 2.5% donkey serum) for 3 hours at room temperature. After washing in tween 0.05% PBS, four times for 10 minutes, sections were incubated with secondary antibody (Alexa Fluor® 546 Donkey Anti-Rabbit IgG (H+L) Antibody, Life technologies, lot: 1504518) diluted 1:200 in PBS with 0.2% Triton X-100 and 2.5% donkey serum for 2 hours at room temperature. Slides were then washed four times for 10 minutes in 0.05% tween PBS followed by one final wash with $dH_2O$. After removing excess fluid, slides were mounted with fluorescent mounting media containing DAPI (Vectashield, Vector Laboratories Ltd., Peterborough, UK) to stain cell nuclei.

For bioimaging, sections were analyzed under an Olympus BX51 upright microscope using ×4, ×10 and ×20 Plan Fln objectives and captured using a Coolsnap ES camera (Photometrics, Tucson, Ariz.) through MetaVue Software (Molecular Devices Ltd. Wokingham, UK). Images were taken under specific band pass filter sets and colour-combined images were used for further processing using ImageJ.

Multi-Electrode Array Recordings

Multi-electrode array recordings were performed on rod opsin treated rd1 mice (n=6) and GFP injected rd1 controls (n=2). Enucleated eyes were placed in a petri dish filled with carboxygenated (95% $CO_2$/5% $CO_2$) aCSF (artificial cerebro-spinal fluid, concentration in mM: 118 NaCl, 25 $NaHCO_3$, 1 $NaH_2PO_4$, 3 KCl, 1 $MgCl_2$, 2 $CaCl_2$, 10 $C_6H_{12}O_6$, 0.5 L-Glutamine). Retinas were then carefully isolated in diffuse red light under a dissecting microscope and mounted, ganglion cell down, onto a 60-channel or 256-channel multi-electrode array (Multi Channel Systems, Reutlingen, Germany). Retinal explants were coupled in place with a weighted dialysis membrane, and continuously perfused with carboxygenated aCSF at 2.2 ml per minute using a peristaltic pump (SC1400, Watson Marlow, UK), and maintained at 32° C. using a Universal Serial Bus temperature controller regulating an inline heater for the inflow of aCSF. Light stimuli (white light) were presented by a customised light engine source (Lumencor, USA). At brightest intensity LEDs were@15 Log photons/cm$^2$/s. A National Instruments card (USB-6229) controlled by programmes written in LabVIEW (Version 8.6, National Instruments, TX, USA) was used to control stimulus duration and intensity by altering LED output and adjusting filter wheel containing neutral-density filters (Cairn Research Ltd). Stimuli were delivered at 2-second pulses of light with 20 s inter-stimulus intervals for 20-30 repeats at ND0 (15 Log photons/cm$^2$/s) to ND4. Data were sampled at 25 kHz frequency during the acquisition of both spontaneous and evoked activity and recorded for off-line sorting using Offline Sorter (Plexon). After removing clear artefacts common to all channels, principal component analyses were used to discriminate single units, identified as distinct clusters of spikes within the principal component space, with a clear refractory period in the interspike interval distribution. Spike sorted, single unit data were then further analysed using Neuroexplorer (Nex Technologies) and MATLAB R2010a (The Mathworks Inc.).

Pupillometry:

Pupillary light reflex (PLR) was measured in were performed on wild-type mice (6), rd1-CAG-GFP mice (n=16), rd1-CAG-hRho mice (n=10) and rd1-grm6-hRho (n=6) at six to eight weeks post injections. Mice were dark-adapted for 1 hour before the recordings. Light stimuli were provided by a quartz halogen lamp and were transmitted along a fiber-optic bundle to an integrating reflective sphere, which provided uniform light at the mouse cornea. Consensual PLR was recorded in un-anaesthetised, lightly scruffed mice, under infra-red conditions with an infra-red sensitive CCD camera fitted with 10× macro lens and an infra-red filter. An intervening shutter controlled stimulus timing. A single trial lasted 20 seconds: 5 seconds light OFF, 10 seconds light ON, 5 seconds light OFF. The intensity of the light was controlled by neutral density (ND) filters and mice were subjected to white light exposures in an ascending intensity series, with individual trials being separated by at least 5 minutes. Photon emission values for NDs in log photons/cm2/s ranged from 15.85 at ND0 to 10.85 at ND5. Pupillary responses were quantified from the video images, by using Virtual Dub and ImageJ software and data were normalised to pupil area immediately preceding the light onset.

In-Vivo Electrophysiology:

In-vivo electrophysiology was performed on wild-type mice (n=2), rd1-CAG-hRho mice (n=7) and rd1-grm6-hRho (n=5). Six weeks post injections and after measurement of PLR, mice were anaesthetised with urethane (intraperitoneal injection 1.7 g/kg; 30% w/v; Sigma Aldrich, Poole, UK). Animals were restrained in a stereotaxic frame (SR-15M; Narishige International Ltd, London, UK) and core body temperature was maintained at 37° C. via a homeothermic heat mat (Harvard Apparatus, Edenbridge, UK). Pupils were dialated with atropine and mineral oil (Sigma Aldrich) was applied to retain corneal moisture. A small craniotomy and durotomy (~1 mm$^2$) were performed directly above each lateral geniculate nucleus (LGN) using stereotaxic coordinates according to mouse atlas (Paxinos and Franklin, 2001; hole centre=bregma: −2.46 mm; midline: −2.8). A 32-channel electrode (NeuroNexus Technologies Inc., MI, USA) was introduced to each LGN in the centre of the hole (medial shank: −2.5 mm relative to midline; depth: −2.6 mm relative to brain surface at 18 degrees angle) for simultaneous recording from both LGNs. Mice were left for 30 min prior to recordings, to dark adapt and to allow neuronal activity to stabilize following electrode insertion. Visual stimuli were provided by UV LED (Thorlab λmax: 405 nm) and delivered via fiber optic to purpose-made eye cones tightly positioned onto each eye to minimise any potential light leak. A National Instruments card (USB-6229) controlled by programmes written in LabVIEW (Version 8.6, National Instruments, TX, USA) was used to control stimulus duration and intensity by altering LED output and adjusting filter wheel containing neutral-density (ND) filters (Cairn Research Ltd). At brightest intensity (ND0) LEDs were@47 W/m2 or 15.4 log photons/cm$^2$/s of effective flux for rod opsin. Data were acquired using a Recorder64 system (Plexon, TX, USA) with signal amplification by a 20× gain AC-coupled headstage (Plexon, TX) followed by preamplifier conditioning providing a total gain of 3500×. Data were high-pass (300 Hz) filtered and time-stamped neural waveforms were digitized simultaneously from all channels at a rate of 40 kHz. Multiunit data was then stored for offline sorting and analysis as for the MEA data described above. At brightest intensity LEDs were 15 Log photons/cm$^2$/s. Stimuli were delivered according to a light protocol consisting of 2 parts. Part 1 included flashes from darkness: 2 s light ON, 20 s light OFF with 10 s offset between each eye. This paradigm was repeated 30× at each ND filter ranging from dimmest (ND3=12.4 log photons/cm$^2$/s) to brightest (ND0=15.4 log photons/cm$^2$/s). Longer stimulus length was also used for more sustained responses: 10 s ON, 30 s OFF with 15 s offset between each eye. The paradigm was repeated 10-20× at ND3 to ND0.

Part 2 of the light protocol involved recording in light adapted conditions where 5-second steps of light were applied to a steady background illumination at Michelson contrast of 96%. There was a 20-second inter-stimulus interval and a 10-second offset between two eyes. This paradigm was repeated ten times.

(Part 2 of the light protocol involved recording in light adapted conditions where increasing light contrasts were applied to a steady background illumination. Michelson contrasts, 33%, 66% and 96% were applied in 5-second steps, with a 20-second inter-stimulus interval and a 10-second offset between two eyes. This paradigm cycle was repeated ten times).

Responses to a naturalistic movie were also recorded. For this, a separate set of recordings (rd1-CAG-hRho mice; n=2 and rd1-grm6-hRho; n=3) was obtained from the dLGN contralateral to the rod opsin treated eye. A different experimental set up was used, involving a digital mirror device projector (DLP® LightCommander™; Logic PD Inc.), in order to maximise the wavelengths used and intensity of the movie. The intrinsic light engine of the projector was replaced with a multispectral LED light source containing four independently controlled LEDs ($\lambda_{max}$ at 405 nm, 455 nm, 525 nm and 630 nm; Phlatlight PT-120 Series (Luminus Devices)). Light from the LEDs was combined by a series of dichroic mirrors (Thorlabs), and directed onto the projector. The movie was presented using Python running PsychoPy Version 1.70.00 software. It featured mice moving around a behavioural arena including movement and looming of different sized objects (subtending visual angles ranging from 0.5° to 36°) at a range of orientations, speeds and contrasts (maximum Michelson contrast=96%). The movie lacked differences in colour, and changes in irradiance across time were minimal (standard deviation of irradiance=5.94%). Previous validations in wild-type mice have shown undetectable responses for presentations of de-focussed versions, indicating that most activity was elicited by changes in spatial patterns and object motion.

Data were acquired using a Recorder64 system (Plexon, TX, USA) with signal amplification by a 20× gain AC-coupled headstage (Plexon, TX) followed by preamplifier conditioning providing a total gain of 3500×. Data were high-pass (300 Hz) filtered and time-stamped neural waveforms were digitized simultaneously from all channels at a rate of 40 kHz, and stored for offline analysis.

To confirm the location of recording sites, the recording electrode was dipped in fluorescent dye (Cell Tracker CM-DiI; Invitrogen) prior to insertion into the brain. After in-vivo recordings, the mouse's brain was removed and post-fixed overnight in 4% paraformaldehyde, prior to cryoprotection for 24 hours in 30% sucrose. 100 μm coronal sections were then cut using a sledge microtome, mounted onto glass slides and cover slipped using Vectashield (Vector Laboratories, Inc.).

Multi-Electrode Array (MEA) Recordings:

Immediately after in-vivo electrophysiology recordings mice were euthanized and enucleated. Eyes were placed in a petri dish filled with carboxygenated (95% $CO_2$/5% $CO_2$) aCSF (artificial cerebro-spinal fluid, concentration in mM: 118 NaCl, 25 $NaHCO_3$, 1 $NaH_2PO_4$, 3 KCl, 1 $MgCl_2$, 2 $CaCl_2$, 10 $C_6H_{12}O_6$, 0.5 L-Glutamine). Retinas were then carefully isolated in diffuse red light under a dissecting microscope and mounted, ganglion cell down, onto a 60-channel multi-electrode array (Multi Channel Systems, Reutlingen, Germany). Retinal explants were coupled in place with a weighted dialysis membrane, and continuously perfused with carboxygenated aCSF at 2.2 ml/minute using a peristaltic pump (SCI400, Watson Marlow, UK), and maintained at 32° C. using a Universal Serial Bus temperature controller regulating an inline heater for the inflow of aCSF. Light stimuli were provided by a customised light engine (Lumencor, USA) to present UV light (Amax: 405 nm). At brightest intensity LEDs were ~15 Log photons/$cm^2$/s. A National Instruments card (USB-6229) controlled by programmes written in LabVIEW (Version 8.6, National Instruments, TX, USA) was used to control stimulus duration and intensity by altering LED output and adjusting filter wheel containing neutral-density filters (Cairn Research Ltd). Stimuli were delivered according to a light protocol as for in-vivo electrophysiology data described above. Data were sampled at 25 kHz frequency during the acquisition of both spontaneous and evoked activity and recorded for off-line analysis.

Behaviour

Currently, commonly used visual discrimination tasks require extensive training, stressful environments, or are based on reflexes rather than goal oriented behaviour. To address these deficits, a simple, open-field based method of assessing vision based on spontaneous behaviour has been developed. Using a modification of the light/dark box (dimensions: length=40 cm width=40 cm and height=30 cm, open top) mice were allowed free movement between two equal arenas (east and west halves) via an opening in the separating wall. Box was made of Perspex glass and its walls were painted white except for the two long sides of each arena, which were kept clear. Two identical infra-red lamps were placed centrally above each arena, to allow visualisation under dark conditions.

The visual stimuli were displayed from two 17-inch flat screen computer monitors, facing clear walls of each arena, using a DualHead2Go Digital Edition external multi-display adapter (Matrox Graphics Inc.). This allowed both the control and the test stimuli to be shown on separate monitors at the same time. A variety of visual stimuli were displayed including a full field uniform light (black, gray and white), full field flicker and a naturalistic movie. These stimuli were created using a custom written programme that allowed the formation of two different stimuli in two different windows simultaneously, whilst retaining the ability to operate both individually. The programme allowed the values of the white (255), black (0) and grey (128) components of the stimuli to be altered to achieve desired brightness and contrast levels.

Behavioural experiments were performed on wild-type mice (5), rd1-CAG-GFP mice (n=6), rd1-CAG-hRho mice (n=6) and rd1-grm6-hRho (n=5). Before the experimental period, mice were handled and habituated to their novel environment over 5 days, at the same time each day, in the following manner: animals were brought into the testing room in their home cages, placed into the experimental box and allowed to move freely with their littermates for 30 minutes.

Following the habituation period, behaviour experiments were conducted over several weeks in a completely dark room at the same time each day. Each group of mice was allowed to undergo only one testing condition per day. On each test day, mice were brought into the testing room in their home cages, allowed to accommodate to the testing room conditions for 30 minutes and then each mouse was tested individually. Mice were placed into the open field box (randomly to east or west half) and allowed to move freely between two arenas. All test trials were recorded under infra-red conditions through a camcorder fitted with an infra-red filter (A=665 nm). The box was thoroughly cleaned with 70% ethanol after each test trial and allowed to air-dry before next mouse was placed into the box.

A recording trial began after 3 minutes of habituation. Each trial run consisted of 5 minutes of control stimulus, following which a test stimulus was presented on a screen facing an arena that contained a mouse at this time point. For dark-adapted experiments, control stimulus consisted of 5 minutes in dark (screens switched on dark; radiance=0.004072 $Wsr^{-1}m^{-2}$, irradiance=0.00132 W/m2) followed by 5 minutes in light (white screen; radiance=0.06526 $Wsr^{-1}m^{-2}$, irradiance=0.116 W/m2) and then 1 minute back in the dark. For light adapted experiments, control stimulus consisted of 5 minutes in uniform gray screen light (gray screen; radiance=0.03342 $Wsr^{-1}m^{-2}$, irradiance=0.0663 W/m2), followed by 5 minutes of full field flicker (flicker screen; radiance=0.03342 $Wsr^{-1}m^{-2}$, irradiance=0.0663 W/m2) followed by 1 minute in the uniform light. For contrast sensitivity experiments, screen outputs were adjusted to allow for different testing contrasts between 2 arenas (Michelson contrasts: 100%, 68.6%, 37.3%, 13.7% and 0% contrast). For the naturalistic movie experiment, control stimulus consisted of 5 minutes of uniform gray light followed by 1 minute of movie presentation and 1 minute back to the control condition. The (colour) movie featured a looming owl.

The recorded trials were stored for off-line analysis using a video tracking software device (EthoVision® XT 10.1 Noldus, Tracksys Ltd., UK). We analysed distance travelled by each mouse in the entire box and outputted results in 30 second bins. The mouse's ability to see the visual stimuli was assessed as a change in locomotor activity during a 1-minute transition period from a control to the test stimulus (i.e. we analysed the distance travelled in 30 s under the control condition just prior to the test stimulus, and the distance travelled in 30 s just after the test stimulus).

Two-way paired t test was used for comparisons within the same group of mice before and after a test stimulus presentation during a 1-minute transition period.

In summary the introduction of human rhodopsin into the inner retinal cells of mice that were blind from a severe retinal degeneration and loss of rod and cone photoreceptors resulted in the restoration of vision as evidenced by a restoration in pupil responses and visual responses in the brain (lateral geniculate nucleus) and retina.

DISCUSSION

In this study it has been demonstrated that the expression of human rod opsin can bestow light sensitivity to blind retinas through a diverse visual code involving ON, OFF, transient and sustained pathways. Robust visual responses were observed in vitro and in vivo under light intensities equivalent of endogenous cone/PR vision and were able to drive sophisticated retinal circuit functions such as contrast detection. Treated blind mice showed restored light-induced locomotor activity under illuminance typical of natural indoor environments and were able to resolve low frequency flicker in light adapted conditions. In addition, with targeted rod opsin treatment mice detected lower contrasts, were able to resolve higher frequency full field flickers and detect naturalistic movie scenes.

Introduction of microbial opsin channels and pumps and chemical photoswitches to surviving retinal neurons can restore light sensitivity. Here, gene therapy can be used to deliver human rod opsin to blind mice. However, one of the main challenges in optogenetic therapy is to achieve stable and effective level of opsin expression in the retina through a clinically relevant delivery method. Current viral delivery methods require invasive sub-retinal injections where transduction is limited to a small portion of the retina at the site of injection. More global transduction could be achieved by injection into the vitreous, a much safer technique that is commonly used in routine ophthalmic practice. However, physical barriers created by the extracellular matrix of retinal cells limit viral transduction from this route. Several novel mutant AAV vectors have emerged (4YF and 7m8) with ability to penetrate deeper into retinal tissue but currently require very high viral titers ($10^{14}$) with potentially high immunogenicity and off target effects. In the present approach intravitreal delivery of AAV2 vector has been used, which has already been proven safe in clinical trials. In addition, a combination of enzymes targeting extracellular matrix proteins that disrupt the physical barriers to viral particles reaching the retina from the vitreous has been identified. Co-injecting these enzymes greatly increases the number and spatial spread of neurones infected by the virus.

In the intact retina mammalian rod opsin is normally found in specialised rod photoreceptors. It belongs to a family of a G-protein coupled receptors (GPCRs) that functions through signalling cascade intermediates. On photoactivation, rod opsin couples to transducin (Gt; a member of Gi/o subfamily) for visual signal transduction (Palczewski, K. G. Annu. Rev. Biochem. (2006) 75, 743-767 in vivo, leading to increase in K+ currents, membrane hyperpolarization and inhibition of neurotransmitter release. A sign inverting synapse between photoreceptors and their second order neurons, bipolar cells, converts this inhibitory response into positive electrical signal that is transmitted via the ganglion cells to the brain for visual percepts.

Opsin channels (ChR) and pumps (HaloR) have been functionally expressed in blind retina leading to depolarization and hyperpolarization respectively. In addition, vertebrate rod opsin has been expressed in cell culture and in vivo outside the retina (cerebellar purkinje cells) and was shown to inhibit neuronal excitability when activated by light (Li X, et al Proc Natl Acad Sci USA. 2005 Dec. 6; 102(49):17816-21; Gutierrez D V, et al J Biol Chem. 2011 July 22; 286(29):25848-58.). However it was now known that a GPCR like rod opsin would be able to function outside native photoreceptors when expressed directly in second or third order neurons (RGCs) and exert its inhibitory action to produce visual signal. It was reasoned that in blind retinas, decoupled from normal photoreceptor input, there is an overall increase in basal activity of surviving output neurons and that rod opsin could act to suppress this 'hyperactivation' and improve the signal to noise ratio in order to support visual discrimination.

Here, it is shown that ectopic rod opsin can express in the inner retinal cells and function outside native photoreceptors. Indeed as predicted it was observed that inhibitory OFF responses in vivo (firing rate decreases with light ON stimulation) in both targeted (35.7% of all light responses) and untargeted (10.8%) rod opsin treatments. These are not normally seen with WT responses and we also did not observe such responses in our in-vitro preparations. However, suprisingly, many positive 'ON responses' were found both in-vitro and in-vivo. Indeed a diverse set of responses were found with both untargeted and targeted treatments including ON sustained, ON transient, and OFF excitatory (firing rate increases with light OFF) responses, as well as in-vivo OFF inhibitory signals. In addition, a small number of ON-OFF responses in-vivo were observed with untargeted treatment. This would suggest that rod opsin can modulate cell behaviour in both depolarising and hyperpolarising light dependent fashion. This would suggest that rod opsin expression in ON bipolar cells is strong enough to drive post-synaptic third order neurons and stimulate amacrine inhibitory loops (AII cells) leading to activation of OFF bipolar cells and therefore double inhibition or excitatory ON responses.

In intact systems visual information is processed through two parallel pathways, ON pathway and OFF pathway. In ON pathway, cells respond to light increments, whereas in OFF pathway cells respond to light decrements. Our restoration of ON and OFF pathways in blind retinas is in support of other studies that have previously specifically targeted ChR and LiGluR to ON-BP cells. However, previous studies using ubiquitous promoters (Lin B, et al Proc Natl Acad Sci USA. 2008 Oct. 14; 105(41):16009-14) or specifically targeting RGC only, have reported electrophysiologically more uniform signals (e.g. sustained ON with ectopic melanopsin) and no simultaneous restoration of both ON and OFF pathways (ChR in RGC drove only ON pathways, whereas HaloR in RGC only OFF pathways). It is possible that expression in RGCs only was not strong enough to directly activate the normal excitatory and inhibitory inputs to the cells. In addition in this case, even with the untargeted treatment, it was found that rod opsin expression in INL cells (likely BP cells), which could explain secondary activation of AII loop and dissection of responses into both inhibitory and excitatory signals.

One of the main advantages of using rod opsin as an optogenetic tool to restore vision lies in its simplicity to provide self-contained photoreception with its ability to use endogenous chromophore (retinal or cis-retinaldehyde) as the natural photoswitch. However, for visual responses, rod opsin requires constant recycling of retinal, which is normally bleached by light. This recycling is thought be dependent upon the intimate contact between the rods and the RPE. Indeed, consistent with previous studies (Li X, et al Proc Natl Acad Sci USA. 2005 Dec. 6; 102(49):17816-21; Gutierrez D V, et al J Biol Chem. 2011 Jul. 22; 286(29): 25848-58), it was found that in vitro rod opsin bleaches readily after light stimulation and it requires constant exogenous supply of chromophore (9-cis retinal) in order to sustain light dependent responses. However, in vivo did not found bleaching to be a significant problem. Importantly, many light responses were robust and repeatable over multiple trials. It is therefore likely that the degenerating retina provides a good endogenous supply of retinal, and in the absence of photoreceptors that normally take it up, rod opsin in inner retinal cells has access to the chromophore recycling by the RPE or Muller cells to produce visual responses.

Another important aspect of rod opsin therapy is its ability to function under physiological light conditions, unlike current strategies based on microbial opsins and synthetic photoswitches that require extremely high light intensities for activation. It was found that that ON and OFF, transient and sustained cell types function in vivo under a dynamic range of light intensities tested ($10^{13}$-$10^{15}$ photons/cm$^2$/s) falling under a range of endogenous cone sensitivity. Previously reported studies used much higher light intensities for activation: LiGluR >$1.7 \times 10^{17}$ photons/cm$^2$/s (Gaub B M, et al 2014, Proc Natl Acad Sci USA. 2014 Dec. 23; 111 (51):E5574-83), ChR >$3 \times 10^{15}$-$10^{17}$ photons/cm$^2$/s (Lagali P S, et al 2008, Nat Neurosci. 2008 June; 11(6):667-75;) HaloR in RGCs >$5.1 \times 10^{18}$ photons/cm$^2$/s (Zhang Y, et al J Neurosci. 2009 Jul. 22; 29(29):9186-96) and HaloR in cone inner segments >$10^{16}$ photons/cm$^2$/s (Busskamp V, et al 2010, Science. 2010 Jul. 23; 329(5990):413-7.). Sensitivity is a factor of intacellular mechanisms and our data suggests that rod opsin can function through GPCR light amplification cascade under low light intensities. This is in contrast to microbial ion channels (ChR2), pumps (HaloR) or photoswitches (LiGluR), which are unable to amplify signals at the protein level.

Further characterisation of the kinetics of restored responses in-vivo showed that the onset, offset and the duration of the light response varied among cell types for both untargeted and targeted approaches. It was found that responses of varied latencies; some fast some slower consistent with previous studies (Caporale N, et al 2011, Mol Ther. 2011 July; 19(7):1212-9; Gaub B M, et al 2014, Proc Natl Acad Sci USA. 2014 Dec. 23; 111(51):E5574-83). Rod opsin light switch is intrinsically fast and slower light responses might be an effect of the dynamics of the intracellular signalling cascade and dependent upon native cell type expressing rod opsin. In addition, slower response onset is likely to be due to non-saturating light input and lower level of expression of rod opsin in some cells. (Some fast rod opsin responses may be through fast kinetics of native mgluR6 receptor cascade in ONBP cells.)

The eye is sensitive over a wide range of light intensities from scotopic (night) to photopic (day) vision. This sensitivity can be measured by minimum threshold intensity necessary to evoke vision. One of the important aspects of our vision is how quickly the eye recovers its sensitivity in dark after bright light exposures (dark adaptation) or more importantly how quickly it adapts to background illumination to be able to discriminate objects in this background (light adaptation). So far most optogenetic studies have studied simple visual stimuli involving light steps from darkness. This is rather an un-natural scenario and in the real world objects have contrast, which is constant and independent of ambient luminance. It was therefore questioned whether the ectopic rod opsin could work under light adapted conditions and conserve the restored visual code against changes in irradiance. Indeed robust dLGN responses were found after increment test light stimulus presentations against a background illumination. (It is possible that the observed robust segregation into ON and OFF pathways is able to facilitate this light adaptation and enhance contrast sensitivity).

Both untargeted and targeted expression was investigated. First a non-selective, untargeted approach with strong pan-neuronal promoter, CAG was used to deliver genes across the surviving inner retina. It was not known which neurons, if any, would express rod opsin and if it would express in one particular type of neuron more than the other or have preference for either ON or OFF pathway or target both equally. It was hoped that the imbalance in expression between ON and OFF pathways would mean that even though some signals would cancel each other out, there would be an overall increase in visual information transmitted to the brain. Advantage of this approach would also mean that the retinal ganglion cells, which survive the longest (Mazzoni F,) J Neurosci 28(52):14282-14292), are also targeted and this approach can be used in late degeneration where bipolar cells become compromised (cronin). Second, it was tested whether restricting the expression to just 'ON' pathway would lead to an improvement in visual signal both electrophysiologically and behaviourally. Rod opsin was specifically targeted to retinal ON bipolar cells using a minimal cell specific promoter Grm6 (Masu M et al., Cell 1995). Striking electrophysiological similarity was observed between untargeted and targeted rod opsin treatments. The recovered code was equally complex and diverse. Response kinetics, the sensitivity and the contrast response were similar for the two treatments. Interestingly, targeted treatment led to more OFF responses (mainly OFF inhibitory). However, there were important differences behaviourally. First, differences in restoration of simple visual function, PLR, was observed. Non-selectively expressed rod opsin restored the drive to the RGC pathway mediating the PLR to near WT level. This is consistent with melanopsin and first generation LiGluR in RGC, which lead to near complete (Lin B, Proc Natl Acad Sci USA. 2008 Oct. 14; 105(41):16009-14.) or partial (Caporale N, et al 2011, Mol Ther. 2011 July; 19(7):1212-9;) restoration of PLR.. Interestingly, when expression was restricted to ON-BP cells this pathway remained largely impaired. It is possible that untargeted expression of rod opsin directly activated ipRGCs (coupling to the Gs/Gq cascade) leading to stimulation, whereas selective expression in ON-BP cells bypassed the direct activation of the pathway and recovery of this non-visual reflex.

What about image forming pathways? Can this visual code that we created be used to improve image-forming vision under physiological light levels? One of the advantages of targeting specifically more distal retinal neurons would be to preserve inner retinal processing, fine-tune restored responses into more coherent signals and achieve better quality vision. So far optogenetic studies have addressed simple visual tasks involving dark-light discrimination and none have reported if the system could track changes against a background illumination or in response to naturalistic scenes. It was found that restored in-vivo responses could support simple dark-light discrimination with both treatments under illumination equivalent of indoor lighting. In addition, mice treated with untargeted and targeted rod opsin treatment could resolve full filed light flicker at 2 Hz against uniform background illumination. In addition it was found that mice with targeted treatment resolved higher frequency flickers including 4 Hz and 10 Hz against uniform background illumination. Moreover, mice with specific expression of rod opsin in ONBP cells were able to detect 4 Hz flicker at a lower contrast level against background illumination (Michelson contrast 66.7%).

Humans excel in processing of natural visual scenes. Despite constantly changing visual scenes our brain is able to transforms complex patterns of light falling on our retina, and extract relevant information into a coherent percept within a few hundred milliseconds. With translational potential in mind, it was questioned whether ectopic rod opsin could drive signals robust enough to preserve many levels of visual processing creating a visual code that mice could use to track natural spatio-temporal modulations in light intensity at levels typical of indoor illumination. Electrophysiologically, with both treatments, it was set out of identify individual neurons that can track changes in light levels over space and time that occur in natural movie scenes. This would suggest that the visual system (with its plasticity) is able to exploit temporally and spatially pooled restored responses carrying simple information on ON and OFF signals and contrast in order to process real natural scenes. In addition, we found that mice post targeted rod opsin treatment increased their locomotory behaviour in response to natural movie scenes. This would suggest that the quality of perceptual vision is improved with targeted compared to untargeted treatment perhaps due to more coherent signal convergence from bipolar cells to RGCs necessary for more complex temporo-spatial discrimination.

In summary, the results show that human rod opsin in surviving inner retinal neurons is a promising strategy to restore vision in retinal degeneration due to loss of photoreceptors and reverse advanced stages of blindness. As a human protein it offers advantages over current microbial-based therapies in terms of ethical and safety concerns. It provides a self-contained photoreceptive strategy that amplifies signal through intracellular cascade and is able to impart improved sensitivity compared to current optogenetic strategies. When ectopically expressed in inner retinal neurons, it generates a diverse visual code based on both ON and OFF responses capable of tracking changes in light intensities over background illumination and in natural movie scenes. Behaviourally, treated blind mice are able to discriminate dark and light and can resolve 2 Hz full field flicker in light adapted conditions under illuminance typical of indoor room lighting. In addition, restricting the expression to ONBP cells, led to improvements in visual percepts in vivo and treated mice were able to resolve higher frequency flickers, detect lower contrast and resolve natural scenes.

The invention claimed is:

1. A method of providing photoreceptor function to an inner retinal cell, comprising
intraocularly administering a therapeutic composition comprising a nucleic acid vector comprising a nucleic acid sequence encoding human rhodopsin or human photopsin, wherein the nucleic acid is under control of a promoter which directs expression to the inner retinal cells;
expressing the nucleic acid sequence in the inner retinal cell; and
augmenting or restoring photoreceptor function of the retina by providing photoreceptor function to the inner retinal cell, wherein the inner retinal cell is an ON-bipolar cell or an OFF-bipolar cell, and wherein the nucleic acid vector is an adeno-associated viral (AAV) vector.

2. The method according to claim 1, wherein the composition is an injectable liquid.

3. The method according to claim 1, wherein the nucleic acid sequence is introduced by intraocular injection.

4. The method according to claim 1, wherein the promoter is selected from the group consisting of L7, thy-1, recoverin, calbindin, GAD-67, Grm6, and Grm6 enhancer-SV40 fusion.

5. The method according to claim 1, wherein the method comprises a step of dilating the pupil of an eye to be treated prior to administering the therapeutic composition.

6. The method according to claim 1, wherein the method further comprises monitoring the vision of a subject who received the therapeutic composition.

7. The method according to claim 1, wherein a photopsin is selected from the group consisting of Long Wavelength Sensitive (OPN1LW) Opsin, Middle Wavelength Sensitive (OPN1MW) Opsin and Short Wavelength Sensitive (OPN1SW) Opsin.

8. The method according to claim 7, wherein the nucleic acid sequence comprises i) the rhodopsin (RHO) gene, or a fragment or derivative thereof, or ii) the Cone *homo sapiens* opsin 1, long wave sensitive OPN1LW gene, or a fragment or derivative thereof; or iii) the Cone *homo sapiens* opsin 1: medium-wave sensitive OPN1MW, or a fragment or derivative thereof; or iv) the Cone *homo sapiens* opsin 1, short-wave-sensitive (OPN1SW), or a fragment or derivative thereof.

9. The method according to claim 3, wherein intra-ocular injection comprises sub-retinal injection or intra-vitreal injection.

10. The method according to claim 4, wherein the promoter is bipolar cell specific promoter Grm6-SV40 for selective targeting of ON-bipolar cells.

11. The method according to claim 5, wherein dilating the pupil of an eye to be treated comprises application of a mydriatic agent.

12. The method according to claim 11, wherein the mydriatic agent is tropicamide and/or phenylephrine.

13. The method according to claim 1, wherein the AAV vector is a serotype 2 vector, AAV 4YF or AAV 7m8.

14. The method according to claim 1, further comprising administering an extracellular matrix degradation enzyme prior to, simultaneously with, or subsequent to administering the therapeutic composition.

* * * * *